US008778359B2

(12) United States Patent
Kaisheva

(10) Patent No.: US 8,778,359 B2

(45) Date of Patent: Jul. 15, 2014

(54) STABLE ANTHRAX VACCINE FORMULATIONS

(75) Inventor: Elizabet Kaisheva, Belmont, CA (US)

(73) Assignee: Emergent BioSolutions Inc., Rockville, MD (US)

( * ) Notice: Subject to any disclaimer, the term of this patent is extended or adjusted under 35 U.S.C. 154(b) by 0 days.

(21) Appl. No.: 13/056,378

(22) PCT Filed: Jul. 30, 2009

(86) PCT No.: PCT/US2009/052279

§ 371 (c)(1), (2), (4) Date: Jun. 8, 2011

(87) PCT Pub. No.: WO2010/053610

PCT Pub. Date: May 14, 2010

(65) Prior Publication Data

US 2011/0229507 A1 Sep. 22, 2011

Related U.S. Application Data

(60) Provisional application No. 61/084,833, filed on Jul. 30, 2008, provisional application No. 61/202,090, filed on Jan. 28, 2009.

(51) Int. Cl.
*A61K 39/07* (2006.01)

(52) U.S. Cl.
USPC .................................... 424/246.1; 424/190.1

(58) Field of Classification Search
None
See application file for complete search history.

(56) References Cited

U.S. PATENT DOCUMENTS

| | | | | |
|---|---|---|---|---|
| 6,284,282 | B1 * | 9/2001 | Maa et al. | 424/499 |
| 6,316,006 | B1 | 11/2001 | Ivins et al. | |
| 6,387,665 | B1 | 5/2002 | Ivins et al. | |
| 7,201,912 | B2 | 4/2007 | Park et al. | |
| 7,223,741 | B2 | 5/2007 | Krieg et al. | |
| 7,261,900 | B2 * | 8/2007 | Leppla et al. | 424/246.1 |
| 7,438,909 | B2 | 10/2008 | Morrow | |
| 7,442,373 | B2 | 10/2008 | Morrow et al. | |
| 2003/0162167 | A1 | 8/2003 | Houghton et al. | |
| 2005/0276756 | A1 | 12/2005 | Hoo et al. | |
| 2005/0281830 | A1 | 12/2005 | Morrow et al. | |
| 2006/0246079 | A1 | 11/2006 | Morrow et al. | |
| 2006/0257426 | A1 | 11/2006 | Baker et al. | |
| 2009/0202553 | A1 | 8/2009 | Morrow et al. | |

OTHER PUBLICATIONS

Dorlands Medical Dictionary for Healthcare Consumers; retrieved from web, one page, no date.*

Stedman's Online Medical dictionary, retrieved from web, one page, no date.*

The American Heritage Dictionary; retrieved from web, one page; no date.*

Stedman's Online Medical Dictionary (http://www.stedmans.com/section.cfm/45) defines invasion.*

Dorland's Medical Dictionary for Healthcare Consumers (http://www.mercksource.com/pp/us/cns/cns_hl_dorlands_split.jsp?pg=/ppdocs/us/common/dorlands/dorland/four/000053439.htm) defines—infection.*

The Online Medical Dictionary (http://cancerweb.ncl.ac.uk/cgi-bin/omd?infection) defines infection.*

Robert Roos, "HHS Cancels VaxGen Anthrax Vaccine Contract," *CIDRAP*, Dec. 20, 2006 (2 pages).

U.S. Securities and Exchange and Exchange Commission Form 10-Q for the quarterly period ending Sep. 30, 2012, Pharmathene, Inc., Nov. 6, 2012 (31 pages).

Bradley K.A., et al., "Identification of the cellular receptor for anthrax toxin", Nature, 414(6860):225-9, Macmillian Magazines Ltd. (2007).

McKevitt, M.T., et al., "Effects of Endogenous D-Alanine Synthesis and Autoinhibition of *Bacillus anthracis* Germination on Inv Vitro and In Vivo Infections", Infection and Immunity, 75(12):5726-5734, American Society for Microbiology (2007).

* cited by examiner

*Primary Examiner* — Patricia A Duffy

(74) *Attorney, Agent, or Firm* — Sterne, Kessler, Goldstein & Fox P.L.L.C.

(57) ABSTRACT

Formulations of anthrax protective antigen are provided that are stable in storage for prolonged periods. Methods of using the formulations to prepare vaccine are also provided. Vaccines comprising the formulations are useful, for example, to protect against anthrax infection.

19 Claims, 15 Drawing Sheets

| | Phos Spike | Pro | Gly Pro NaCl | Gly | Alanine | Citrate + NaCl | PBS | 50mM Spike |
|---|---|---|---|---|---|---|---|---|
| 4 Weeks | 10 | 103 | 61 | 89 | 84 | 29 | 26 | 8 |
| 6 Weeks | 4 | | 39 | 60 | 60 | 21 | 28 | 0 |
| 8 Weeks | 0 | 87 | 39 | 58 | 58 | 0 | 6 | 0 |
| 12 Weeks | 0 | 87 | | 38 | 58 | 0 | 0 | 0 |

EBS-121v2

| Sample | MLA Activity (% of Reference) |
|---|---|
| Ala (t=0 months) | 159% |
| Ala (t=12 months) | 99% |
| Gly (t=0 months) | 125% |
| Gly (t=12 months) | 103% |
| Pro (t=0 months) | 123% |
| Pro (t=12 months) | 75% |
| Phosphate (t=0 months) | 104% |
| Phosphate (t=12 months) | 82% |

EBS-13104

*Figure 10. While the alanine and glycine based formulations have the highest 3B6 to 15F7 ratio at 25° C, all four formulations are similar when stored at 2-8° C for 12 months*

Figure 13.

| Group Number | Vaccine | No of Mice | Dilution Factor | Blood Collection (day) |
|---|---|---|---|---|
| 1 | rPA102-ALA (Fresh) | 15 | 4 | 0, 21, 28 |
| 2 | rPA102-ALA (Aged) | 15 | 4 | 0, 21, 28 |
| 3 | rPA102-PRO (Fresh) | 15 | 4 | 0, 21, 28 |
| 4 | rPA102-PRO (Stored) | 15 | 4 | 0, 21, 28 |
| 5 | rPA102-GLY (Fresh) | 15 | 4 | 0, 21, 28 |
| 6 | rPA102-GLY(Stored) | 15 | 4 | 0, 21, 28 |
| 7 | AVA | 15 | 2 | 0, 21, 28 |

EBS-182

Figure 14.

| Group Number | Vaccine | No of Mice | Dilution Factor | Blood Collection (day) |
|---|---|---|---|---|
| 1 | rPA102-ALA (Fresh) | 15 | 8 | 0, 21, 28 |
| 2 | rPA102-ALA (Aged) | 15 | 8 | 0, 21, 28 |
| 3 | rPA102-PRO (Fresh) | 15 | 8 | 0, 21, 28 |
| 4 | rPA102-PRO (Stored) | 15 | 8 | 0, 21, 28 |
| 5 | rPA102-GLY (Fresh) | 15 | 8 | 0, 21, 28 |
| 6 | rPA102-GLY(Stored) | 15 | 8 | 0, 21, 28 |
| 7 | AVA | 15 | 4 | 0, 21, 28 |

EBS-181

| Buffer | Preservative Concentration | | | |
|---|---|---|---|---|
| 220 mM alanine , 25 mM sodium phosphate, 0.01% PS80 pH 7.0 plus 2-phenoxyethanol | 10,000 ppm | 5,000 ppm | 1,000 ppm | 500 ppm |
| 220 mM alanine , 25 mM sodium phosphate, 0.01% PS80 pH 7.0 plus benzethonium chloride | 100 ppm | 50 ppm | 10 ppm | 5 ppm |
| 250 mM glycine, 25 mM sodium phosphate, 0.01% PS80 pH 7.0 plus 2-phenoxyethanol | 10,000 ppm | 5,000 ppm | 1,000 ppm | 500 ppm |
| 250 mM glycine , 25 mM sodium phosphate, 0.01% PS80 pH 7.0 plus benzethonium chloride | 100 ppm | 50 ppm | 10 ppm | 5 ppm |

EBS-T301

Figure 22.

| Additional FDP Comparability Assays for Development | Purpose of Assay |
|---|---|
| Mouse TNA | Determination of immunogenicity |
| Peptide Digest with LC-MS and MS-MS | Sequence information and information on deamidation |
| Epitope exposure | Protein structural information regarding protein folding and exposure of neutralizing vs. non-neutralizing epitopes |
| Front Faced Fluorescence | Protein structural information regarding protein folding |
| SDS-PAGE | Determination of gross degradation of primary structure |
| Western blot | Determination of gross degradation of primary structure |

Figure 23.

| Formulation | Storage Conditions | Time points (Months) | Assays |
|---|---|---|---|
| A | 2-8° C | 1,3,6,9,12,18,24,36,48 | |
| | 24-26° C | 1,3,6 | |
| B | 2-8° C | 1,3,6,9,12,18,24,36,48 | Free rPA102, pH, Appearance, Mouse TNA, Aluminum, SDS-PAGE, Western Blot, Epitope ratio (3B6 to 15F7), Peptide digest/MS |
| | 24-26° C | 1,3,6 | |
| C | 2-8° C | 1,3,6,9,12,18,24,36,48 | |
| | 24-26° C | 1,3,6 | |
| D | 2-8° C | 1,3,6,9,12,18,24,36,48 | |
| | 24-26° C | 1,3,6 | |
| E | 2-8° C | 1,3,6,9,12,18,24,36,48 | |
| | 24-26° C | 1,3,6 | |

STABLE ANTHRAX VACCINE FORMULATIONS

CLAIM OF PRIORITY

This application is a National Phase Application of International Application Number PCT/US2009/052279, filed Jul. 30, 2009, and claims the benefit of priority of U.S. provisional application Nos. 61/084,833, filed Jul. 30, 2008 and 61/202,090, filed Jan. 28, 2009, the entire disclosures of which are incorporated by reference.

GOVERNMENT RIGHTS

This invention may have been made with government support in the form of Department of Health and Human Services Contract Award Number HHSO10020050001C awarded to VaxGen, Inc. on Nov. 4, 2004 and National Institutes of Allergy and Infectious Disease Contract Award Number N01-A1-30053 award to VaxGen, Inc. on Sep. 30, 2003. The US Government may have certain rights in this invention.

FIELD OF THE INVENTION

The present invention relates to stable formulations of anthrax vaccines, methods of preparing stable formulations, and methods of using those formulations.

BACKGROUND OF THE INVENTION

Anthrax is a well-known infectious disease caused by a Gram-positive bacterium, *Bacillus anthracis* (*B. anthracis*). Among the three types of anthrax infection (cutaneous, gastrointestinal, and inhalation), cutaneous anthrax is the most common and is relatively easily treatable with various antibiotics. The other two types of anthrax infections are rare, but usually fatal even with aggressive anti-microbial therapy.

The major virulence factor, anthrax toxin, is composed of three proteins: protective antigen (PA, 83 kilo Dalton, kDa), edema factor (EF, 89 kDa), and lethal factor (LF, 90 kDa). The toxin components act in the binary combinations of PA+EF (edema toxin), and PA+LF (lethal toxin). PA is a cell receptor-binding protein and delivers the other two proteins (EF and LF) into the cytosol of infected cells.

The most effective known method for preventing anthrax is vaccination. The current and only FDA-approved anthrax vaccine in the United States (produced by Emergent BioSolutions Inc. under the trademark BioThrax® Anthrax Vaccine Adsorbed) is produced from a sterile cell-free filtrate from an avirulent *B. anthracis* V770-NP1-R strain. The licensed anthrax vaccine is also called Anthrax Vaccine Adsorbed (or AVA). The vaccine primarily consists of PA, and aluminum hydroxide is used as an adjuvant. The vaccine was developed during the 1950s and 1960s and is licensed by the FDA to Emergent BioSolutions Inc. The vaccine is safe, showing less than 0.06% systemic reactions. The ability of the vaccine to elicit an immune response in humans is well-documented. The BioThrax® Anthrax Vaccine Adsorbed vaccine is currently licensed for six doses over 18 months followed by annual boosts.

Although the BioThrax® Anthrax Vaccine Adsorbed vaccine is effective and safe, new immunogenic compositions for preparing a vaccine that protects a subject against a lethal *B. anthracis* infection using recombinant technologies are under development. Recombinant vaccine protein components could allow the use of new types of adjuvants that could elicit enhanced or more diverse immune responses. Because protective antigen (PA) is the common factor required for both the actions of LF and EF, it is often used to prepare vaccines for anthrax. Recombinant PA (rPA), however, does not elicit a strong protective response against the disease and there have also been issues with its stability. For example, the FDA in November 2006 placed a clinical trial using VaxGen's rPA102 vaccine on hold because of stability issues with the vaccine formulation. Accordingly, there is a need for a rPA anthrax vaccine that has improved stability.

SUMMARY OF THE INVENTION

The present invention provides vaccine formulations that exhibit improve stability. In one embodiment, the disclosure provides formulations of PA (e.g., rPA) that have improved storage characteristics. The formulations vary in their exact composition, but share in common that they provide improved PA stability, as can be measured, for instance, by one or more assays set forth in the disclosure. Those formulations may be used in the preparation of vaccines that provide protection from anthrax infection. In another embodiment, the formulations of the invention can be used for the preparation of vaccines for treatment of an anthrax infection (i.e., administered to a subject post-exposure).

Thus, in one embodiment, the invention provides a stable vaccine for the prevention or treatment of a *Bacillus anthracis* infection or related condition comprising: a) a *B. anthracis* protective antigen protein; and b) a proline formulation buffer. In general, the proline formulation buffer comprises about 50 mM to about 500 mM proline. In some embodiments, the proline formulation buffer further comprises about 10 to about 250 mM NaCl. In one particular embodiment, the proline formulation buffer comprises about 150 mM proline, about 100 mM NaCl, about 25 mM sodium phosphate and about 0.01% polysorbate 80.

In another embodiment, the proline formulation buffer further comprises glycine and/or alanine. For example, the proline formulation buffer may comprise about 100 mM proline, about 50 mM glycine, about 100 mM NaCl, about 25 mM sodium phosphate and about 0.01% polysorbate 80.

In each embodiment, the proline formulation buffer is at about pH 6.2-8.0. In some embodiments, the proline formulation buffer is at about pH 7.0. In other embodiments, the proline formulation buffer is at about pH 7.4.

The invention also provides a stable vaccine for the prevention or treatment of a *Bacillus anthracis* infection or related condition comprising: a) a *B. anthracis* protective antigen protein; and b) an alanine formulation buffer. In general, the alanine formulation buffer comprises about 50 to 500 mM alanine. In certain embodiments, the alanine formulation buffer comprises about 220 mM alanine, about 25 mM sodium phosphate and about 0.01% polysorbate 80.

In another embodiment, the alanine formulation buffer further comprises glycine and/or proline.

In each embodiment, the alanine formulation buffer is at about pH 6.2-8.0. In certain embodiments, the alanine formulation buffer is at about pH 7.0. In other embodiments, the alanine formulation buffer is at about pH 7.4.

The invention also provides a stable vaccine for the prevention or treatment of a *Bacillus anthracis* infection or related condition comprising: a) a *B. anthracis* protective antigen protein; and b) a glycine formulation buffer. In general, the glycine formulation buffer comprises about 50 mM to about 500 mM glycine. In certain embodiments, the glycine formulation buffer comprises about 250 mM glycine, about 25 mM sodium phosphate and about 0.01% polysorbate 80.

In another embodiment, the glycine formulation buffer further comprises proline and/or alanine.

In each embodiment, the glycine formulation buffer is at about pH 6.2-8.0. In certain embodiments, the glycine formulation buffer is at about pH 7.0. In other embodiments, the glycine formulation buffer is at about pH 7.4.

When the formulation is prepared as a vaccine, the formulation generally further comprises a pharmaceutically acceptable adjuvant. Adjuvants may be chosen from alhydrogel, ImmunoStimulatory Sequences (ISS, CpG), or calcium phosphate. In many embodiments, the adjuvant is Alhydrogel.

The source of the protective antigen may vary. Thus, in some embodiments, the *B. anthracis* protective antigen protein is produced from an asporogenic *B. anthracis* bacterium. In some embodiments, the asporogenic *B. anthracis* bacterium is a ΔSterne-1(pPA102) CR4 strain of bacteria.

In many embodiments, the *B. anthracis* protective antigen protein comprises SEQ ID NO: 1. In some embodiments, however, the *B. anthracis* protective antigen protein comprises a deletion of residues 162-167, a substitution of isoleucine for serine at residue 168, a deletion of residues 304-317, and a substitution of glycine for serine at residue 319 of SEQ ID NO: 1.

As mentioned, the formulation and the resulting vaccines are stable. Thus, in some embodiments the vaccine is stable at temperatures below 25° C. for at least 6 months. In other embodiments, the vaccine is stable at temperatures below 25° C. for at least 1 year. In still other embodiments, it is stable at temperatures below 25° C. for at least 1.5 years. And in yet other embodiments, the formulations and vaccine are stable at temperatures below 25° C. for at least 2 years.

The formulations and vaccines are also stable at lower temperatures. For example, in many embodiments they are stable at about 2-8° C. for at least 6 months. Often, they are stable at about 2-8° C. for at least 1 year. They may also be stable at about 2-8° C. for at least 1.5 years, or even at least 2 years.

The present invention includes methods of preventing and treating an anthrax infection comprising administering to a subject a pharmaceutically effective amount of one of the vaccines of the invention. In another embodiment, the invention includes methods of inducing an immune response in a subject comprising administering to the subject a vaccine of the invention.

The present invention includes assays developed that are useful for determining the stability of a vaccine composition.

BRIEF DESCRIPTION OF THE DRAWINGS

FIG. 13. Study design summary for experiment 1.

FIG. 14. Study design summary for experiment 2.

FIG. 22. Comparability study between the multi-dose formulation containing preservative and the single-dose formulation without preservative.

FIG. 23. Stability plan and testing for formulations containing preservatives.

FIG. 27A presents the $ED_{50}$. FIG. 27B presents the $NF_{50}$.

DETAILED DESCRIPTION

Figure 1:
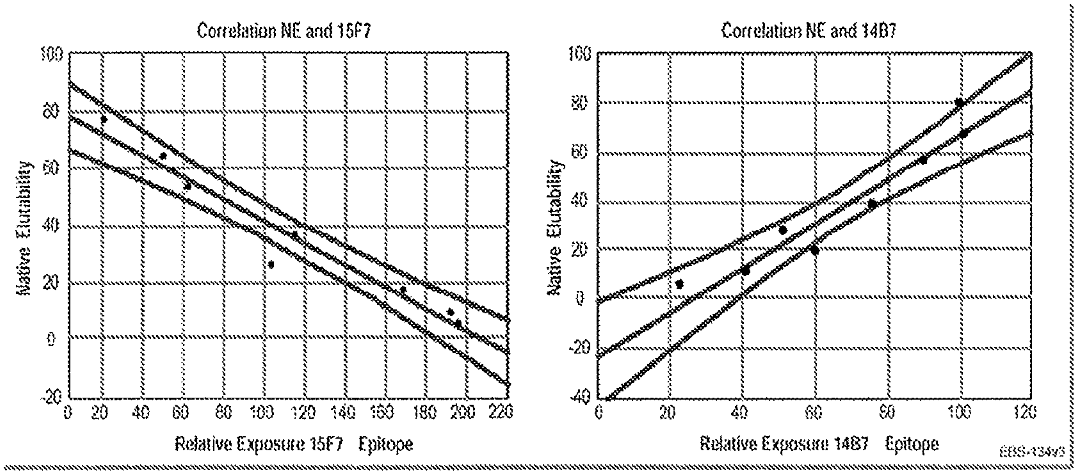
FIG. 1. Results from the FCIA assay demonstrate a strong positive correlation between the exposure of the native epitope (bound by 14B7) and the ability to elute rPA102 from Alhydrogel. Results also show a strong negative correlation between the exposure of a non-native epitope (bound by 15F7) and an inability to elute rPA102 from Alhydrogel.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in the application, the definition that appears in this application controls.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise.

I. DEFINITIONS

In order that the present invention may be more readily understood, certain terms are first defined. Additional definitions are set forth throughout the detailed description.

Protective antigen (PA)—the component of anthrax toxin (approx 83 kDa) that contains the receptor-binding and translocation domains. One example of a full length PA amino acid sequence is:

(SEQ ID NO: 1)

```
EVKQENRLLNESESSSQGLLGYYFSDLNFQAPMVVTSSTTGDLSIPSSEL
ENIPSENQYFQSAIWSGFIKVKKSDEYTFATSADNHVTMWVDDQEVINKA
SNSNKIRLEKGRLYQIKIQYQRENPTEKGLDFKLYWTDSQNKKEVISSDN
LQLPELKQKSSNSRKKRSTSAGPTVPDRDNDGIPDSLEVEGYTVDVKNKR
TFLSPWISNIHEKKGLTKYKSSPEKWSTASDPYSDFEKVTGRIDKNVSPE
ARHPLVAAYPIVHVDMENIILSKNEDQSTQNTDSQTRTISKNTSTSRTHT
SEVHGNAEVHASFFDIGGSVSAGFSNSNSSTVAIDHSLSLAGERTWAETM
GLNTADTARLNANIRYVNTGTAPIYNVLPTTSLVLGKNQTLATIKAKENQ
LSQILAPNNYYPSKNLAPIALNAQDDFSSTPITMNYNQFLELEKTKQLRL
DTDQVYGNIATYNFENGRVRVDTGSNWSEVLPQIQETTARIIFNGKDLNL
VERRIAAVNPSDPLETTKPDMTLKEALKIAFGFNEPNGNLQYQGKDITEF
DENFDQQTSQNIKNQLAELNATNIYTVLDKIKLNAKMNILIRDKRFHYDR
NNIAVGADESVVKEAHREVINSSTEGLLLNIDKDIRKILSGYIVEIEDTE
GLKEVINDRYDMLNISSLRQDGKTFIDFKKYNDKLPLYISNPNYKVNVYA
VTKENTIINPSENGDTSTNGIKKILIFSKKGYEIG.
```

SEQ ID NO: 1 is the amino acid sequence of rPA102 which is expressed from plasmid pPA102. During secretion of rPA102 from *B. anthracis* ΔSterne-1(pPA102)CR4 into the extracellular space, the first 29 amino acids (the signal peptide) are removed yielding the mature rPA protein of 735 amino acids (82,674 Da). The mature rPA sequence is underlined.

The rPA102 amino acid sequence is but one example of one particular anthrax protein within the scope of the invention. Additional amino acid sequences of PA proteins, including native proteins, from various strains of anthrax are known in the art and include, for example, GenBank Accession Nos: NP_652920.1, ZP_02937261.1, ZP_02900013.1, ZP_02880951.1 which are incorporated by reference. Various fragments, mutations, and modifications in PA to reduce its toxicity or to improve its expression characteristics are also known, such as those described elsewhere in the specification, as are various fusion proteins. Those fragments, mutants, and fusion proteins are included in the term "PA" unless the context or text clearly indicates that those forms are excluded. Where indicated, PA fragments, mutants, and fusion proteins (whether with full length PA or a PA fragment) are those that elicit an antisera that is active in the toxin neutralization assay (TNA).

Stable Vaccine: the formulations of the present invention are stable compared to a control PA formulation in which the buffer consists of 20 mM sodium phosphate/20 mM Tris/150 mM sodium chloride and 0.01% polysorbate 80 (PS80), pH 7.4. With the exception of the buffer, the control PA formulation is similar or identical to the stable vaccine (i.e., PA and other components of the vaccine are the same). As used herein, "stable" or "stability" can be measured using any one or more of the assays described herein, including the working examples, as well as assays known in the art that are used to measure activity, potency and/or peptide degradation. A stable vaccine as used herein is a vaccine that exhibits no or little decrease in activity and/or potency and/or degradation over time. In one embodiment, a stable vaccine exhibits substantially less of a decrease in activity and/or potency and/or degradation over time compared to a control PA formulation. By "substantially less" it is meant that there is at least a 1 fold, 2 fold, 3 fold, 4 fold, 5 fold or 10 fold or more difference in activity and/or potency and/or degradation between the stable vaccine and control PA formulation.

Storage: refers to placement of a PA formulation at a specified temperature (+/− at most 5° C.) for a specified period of time. Storage generally starts at least within 6 hours following the initial preparation of the formulation, unless otherwise indicated by the context or clearly specified.

Control Formulation: A formulation of PA from *Bacillus anthracis* in 20 mM sodium phosphate/20 mM Tris/150 mM sodium chloride and 0.01% polysorbate PS80, pH 7.4 The concentration of PA will be the same (or within +/−5%) as that of the comparison formulation. The source (e.g., recombinant or non-recombinant material, production lot, etc.) of PA will also be the same as the source of PA in the comparison formulation.

Formulation Buffer: An amino acid buffer comprising alanine, glycine and/or proline that stabilizes an rPA vaccine. Although the term "buffer" is used herein, the term should be understood to be equivalent to the term "excipient" when used to describe the stabilizing properties of the amino acids on a rPA vaccine.

II. FORMULATIONS OF STABLE PROTECTIVE ANTIGEN

The invention provides formulations that improve the stability of *Bacillus anthracis* protective antigen (PA) during storage. Improvement in the storage characteristics of PA can be measured, for instance, either by evaluating the extent of protein degradation, the retention of functional activity, or the percentage of protein in native conformation at different time points and different storage temperatures. Measurements for determining whether a PA formulation has improved storage characteristics are made compared to a control formulation, such as a PA formulation in which the buffer consists of 20 mM sodium phosphate/20 mM Tris/150 mM sodium chloride and 0.01% polysorbate 80, pH 7.4.

In one embodiment, the formulation buffer of the invention comprises one or more free amino acids. In other words, in one embodiment of the invention, the PA vaccines of the invention comprise one or more amino acid excipients. Often, the amino acid is chosen from alanine, glycine, proline, or combinations thereof. In some embodiments, the amino acid is alanine. In other embodiments, it is glycine. In still other embodiments, the amino acid is proline. And in yet other embodiments, the formulation comprises a combination of glycine and proline, or glycine and alanine, or proline and alanine. In certain embodiments of the invention, the formulation comprises a single free amino acid chosen from alanine, glycine, proline. That is, although the formulation may comprise additional ingredients, the amino acids in the formulation consist of either alanine, glycine, or proline.

The amino acid of the formulation is usually present in the range of about 50 mM to about 500 mM. In some embodiments, the amino acid is present in the formulation at about 50 mM to about 400 mM, or about 50 mM to about 300 mM, or about 50 mM to about 200 mM, or about 50 mM to about 100 mM. In other embodiments, it is present at about 100 mm to about 500 mM, at about 100 mM to about 400 mM, at about 100 mM to about 300 mM, or at about 100 mM to about 200 mM. In still other embodiments, the amino acid is present in the formulation at about 200 mm to about 500 mM, at about 200 mM to about 400 mM, or at about 300 mM to about 300 mM. In yet other embodiments, it is present at about 300 mM to about 500 mM, or about 300 mM to about 400 mM, or even at about 400 mM to about 500 mM. Of course, it is also possible for the amino acid to be present in the formulation at about 50 mM, about 100 mM, about 150 mM, about 200 mM, about 210 mM, about 220 mM, about 230 mM, about 240 mM, about 250 mM, about 260 mM, about 270 mM, about 280 mM, about 290 mM, about 300 mM, about 350 mM, about 400 mM, about 450 mM, or at about 500 mM.

The pH of the formulation may also vary. In general, it is between about pH 6.2 to about pH 8.0. In some embodiments, the pH is about 6.2, about 6.4, about 6.6, about 6.8, about 7.0, about 7.2, about 7.4, about 7.6, about 7.8, or about 8.0. Of course, the pH may also be within a range of values. Thus, in some embodiments the pH is between about 6.2 and about 8.0, between about 6.2 and 7.8, between about 6.2 and 7.6, between about 6.2 and 7.4, between about 6.2 and 7.2, between about 6.2 and 7.0, between about 6.2 and 6.8, between about 6.2 and about 6.6, or between about 6.2 and 6.4. In other embodiments, the pH is between 6.4 and about 8.0, between about 6.4 and 7.8, between about 6.4 and 7.6, between about 6.4 and 7.4, between about 6.4 and 7.2, between about 6.4 and 7.0, between about 6.4 and 6.8, or between about 6.4 and about 6.6. In still other embodiments, the pH is between about 6.6 and about 8.0, between about 6.6 and 7.8, between about 6.6 and 7.6, between about 6.6 and 7.4, between about 6.6 and 7.2, between about 6.6 and 7.0, or between about 6.6 and 6.8. In yet other embodiments, it is between about 6.8 and about 8.0, between about 6.8 and 7.8, between about 6.8 and 7.6, between about 6.8 and 7.4, between about 6.8 and 7.2, or between about 6.8 and 7.0. In still other embodiments, it is between about 7.0 and about 8.0, between about 7.0 and 7.8, between about 7.0 and 7.6, between about 7.0 and 7.4, between about 7.0 and 7.2, between about 7.2 and 8.0, between about 7.2 and 7.8, between about 7.2 and about 7.6, between about 7.2 and 7.4, between about 7.4 and about 8.0, about 7.4 and about 7.6, or between about 7.6 and about 8.0.

In some embodiments, the formulation further comprises one or more additional ingredients that are not free amino acids. For example, the formulation may include one or more salts, such as sodium chloride, sodium phosphate, or a combination thereof. In general, each salt is present in the formulation at about 10 mM to about 200 mM. Thus, in some embodiments, any salt that is present is present at about 10 mM to about 200 mM, about 20 mM to about 200 mM, about 25 mM to about 200 mM, at about 30 mM to about 200 mM, at about 40 mM to about 200 mM, at about 50 mM to about 200 mM, at about 75 mM to about 200 mM, at about 100 mM to about 200 mM, at about 125 mM to about 200 mM, at about 150 mM to about 200 mM, or at about 175 mM to about 200 mM. In other embodiments, any salt that is present is present at about 10 mM to about 175 mM, about 20 mM to about 175 mM, about 25 mM to about 175 mM, at about 30 mM to about 175 mM, at about 40 mM to about 175 mM, at about 50 mM to about 175 mM, at about 75 mM to about 175 mM, at about 100 mM to about 175 mM, at about 125 mM to about 175 mM, or at about 150 mM to about 175 mM. In still other embodiments, any salt that is present is present at about 10 mM to about 150 mM, about 20 mM to about 150 mM, about 25 mM to about 150 mM, at about 30 mM to about 150 mM, at about 40 mM to about 150 mM, at about 50 mM to about 150 mM, at about 75 mM to about 150 mM, at about 100 mM to about 150 mM, or at about 125 mM to about 150 mM. In yet other embodiments, any salt that is present is present at about 10 mM to about 125 mM, about 20 mM to about 125 mM, about 25 mM to about 125 mM, at about 30 mM to about 125 mM, at about 40 mM to about 125 mM, at about 50 mM to about 125 mM, at about 75 mM to about 125 mM, or at about 100 mM to about 125 mM. In some embodiments, any salt that is present is present at about 10 mM to about 100 mM, about 20 mM to about 100 mM, about 25 mM to about 100 mM, at about 30 mM to about 100 mM, at about 40 mM to about 100 mM, at about 50 mM to about 100 mM, or at about 75 mM to about 100 mM. In yet other embodiments, any salt that is present is present at about 10 mM to about 75 mM, about 20 mM to about 75 mM, about 25 mM to about 75 mM, at about 30 mM to about 75 mM, at about 40 mM to about 75 mM, or at about 50 mM to about 75 mM. In still other embodiments, any salt that is present is present at about 10 mM to about 50 mM, about 20 mM to about 50 mM, about 25 mM to about 50 mM, at about 30 mM to about 50 mM, or at about 40 mM to about 50 mM. In other embodiments, any salt that is present is present at about 10 mM to about 40 mM, about 20 mM to about 40 mM, about 25 mM to about 40 mM, at about 30 mM to about 40 mM, at about 10 mM to about 30 mM, at about 20 mM to about 30, at about 25 mM to about 30 mM, at about 10 mM to about 25 mM, at about 20 mM to about 25 mM, or at about 10 mM to about 20 mM. In particular embodiments, the sodium chloride is present in the formulation at about 100 mM. In particular embodiments, the sodium phosphate is present in the formulation at about 25 mM.

In one embodiment of the invention, the vaccine composition comprises at least about 25 μg PA. In another embodiment of the invention, the vaccine comprises at least 50 μg PA. In yet another embodiment, the vaccine comprises at least 75 μg PA.

Formulations of the invention are stable in that their characteristics change little over a given period of time at a defined temperature. In general, formulations of the invention are stable for at least about a month. In some embodiments, the formulations are stable for at least about 6 weeks, at least about 2 months, at least about 4 months, at least about 6 months, at least about 8 months, at least about 10 months, at least about 12 months (1 year), at least about 14 months, at least about 16 months, at least about 18 months (1.5 years), at least about 20 months, at least about 22 months, at least about 24 months (2 years), at least about 26 months, at least about 28 months, at least about 30 months, at least about 32 months, at least about 34 months, at least about 36 months (3 years), at least about 38 months, at least about 40 months, at least about 42 months, at least about 44 months, at least about 46 months or at least about 48 months (4 years).

The temperatures over which a formulation is stable are generally below about 30° C. In some embodiments, the formulation's stability is in reference to a temperature below about 25° C., about 20° C., about 15° C., about 10° C., about 8° C., about 5° C., about 4° C., or about 2° C. Thus, in some embodiments, the temperature is in the range of about 25° C. to about 2° C., about 20° C. to about 2° C., about 15° C. to about 2° C., about 10° C. to about 2° C., about 8° C. to about 2° C., or about 5° C. to about 2° C. In other embodiments, the temperature is in the range of about 25° C. to about 5° C., about 20° C. to about 5° C., about 15° C. to about 5° C., about 10° C. to about 5° C., or about 8° C. to about 5° C. In still other embodiments, the temperature is in the range of about 25° C. to about 8° C., about 20° C. to about 8° C., about 15° C. to about 8° C., or about 10° C. to about 8° C. In yet other embodiments, the temperature is in the range of about 25° C. to about 10° C., about 20° C. to about 10° C., about 15° C. to about 10° C., about 25° C. to about 15° C., about 20° C. to about 15° C., or about 25° C. to about 20° C.

Formulations of the invention may further comprise a solubilizing agent such as a nonionic detergent. Such detergents include, but are not limited to, polysorbate 80 (Tween® 80), TritonX100 and polysorbate 20.

III. STABILITY ASSAYS

The invention provides formulations that improve the stability of *Bacillus anthracis* protective antigen (PA) during storage. Improvement in the storage characteristics of PA can be measured either by evaluating the extent of protein degradation, the retention of functional activity, or the percentage of protein in native conformation at different time points and different storage temperatures. Measurements for determining whether a PA formulation has improved storage characteristics are made compared to a control formulation, such as a PA formulation in which the buffer consists of 20 mM sodium phosphate/20 mM Tris/150 mM sodium chloride and 0.01% polysorbate 80, pH 7.4. Various assays for measuring stability exist including, but not limited to, various assays described herein.

In order to properly evaluate the protein and understand the degradation pathways, several additional assays were developed. These assays include:

Native Elutability (NE). This assay is used to estimate the fraction of PA that can be recovered from the adjuvant under non-denaturing conditions. Results from the native elutability assay are reported as relative to the native elutability for each specific formulation at time=0. A decrease in NE is interpreted as due either to conformational changes in PA or to deamidation, resulting in increased binding to the adjuvant.

Biochemical Activity. This assay is based on the macrophage lysis assay (MLA) and is used as a functional cell based bioassay that measures the cytotoxicity of lethal toxin. Lethal toxin is formed by mixing lethal factor with either reference PA or the test PA. The assay requires the elution of active PA from the adjuvant. A decrease in activity is interpreted as a change in the native conformation of the PA eluted from the adjuvant.

Flow Cytometric Immunoassay (FCIA). This assay measures the exposure of different PA epitopes. The FCIA assay is based on the binding of monoclonal antibodies to specific epitopes. The test antibodies include 14B7, which blocks cell-receptor binding and indicates that PA is in its native conformation. Antibody 15F7 has been shown to bind epitopes of unfolded PA and therefore can detect non-native conformation. The assay can be performed while the PA is bound to an adjuvant. A decrease in the ratio of signal from the 14B7 antibody relative to signal from the 15F7 antibody is interpreted as a change in the PA native conformation.

Peptide map analysis. RP-HPLC/ESI-MS provides information on deamidation of the PA.

Front Faced Fluorescence (FFF). This assay measures the intrinsic tryptophan fluorescence and provides information on protein tertiary structure changes. Changes in tryptophan exposure to the environment are interpreted as conformational changes of the PA, either free or bound to an adjuvant.

Additional details and yet other assays are described in the Examples section.

IV. SOURCES OF PROTECTIVE ANTIGEN

The invention provides methods of preparing stable formulations of protective antigen from *Bacillus anthracis*. In general, the formulations are more stable in storage than is a control formulation using the same source of PA.

Methods of producing PA for inclusion in the formulations of the invention are known in the art and are described, for example in U.S. Pat. No. 7,201,912, to Park and Giri, U.S. Pat. No. 6,387,665 to Ivins et al., U.S. Pat. No. 6,316,006 to Worsham et al., and U.S. Pat. No. 7,261,900 to Leppla et al., each of which is incorporated by reference in its entirety. For example, as described in U.S. Pat. No. 7,201,912, pBP103 is an expression vector for full-length, wild-type rPA. The PA sequence from pBP103 is identical to that of wild-type PA.

The present invention includes formulations comprising PA expressed in *B. anthracis*, including expression in both sporulating and non-sporulating strains of *B. anthracis*. For instance, the PA can be derived from non-sporulating *B. anthracis* strain ΔSterne-1 (pPA102)CR4 (i.e., rPA102). See, for instance, U.S. Pat. No. 6,316,006 and U.S. Pat. No. 6,387,665, both to Ivins et al., each of which is herein incorporated by reference in its entirety.

The formulations of the invention may also include *B. anthracis* PA expressed by a heterologous organism. For instance, the invention includes PA expressed in *E. coli*.

In addition, various PA fragments, mutants, and fusion proteins have also been described and can be used in the current formulations. For example, PA may be modified to lack a functional binding site, thereby preventing PA from binding to either Anthrax Toxin Receptor (ATR) (see Bradley, K. A., et al (2001)) to which native PA binds, or to native LF. By way of example, a modification made within or near to amino acid residues 315-735 or within or near to residues 596-735 of Domain 4 may render PA incapable of binding to ATR. Alternatively (or in addition), the PA furin cleavage site "RKKR" (SEQ ID NO: 2), which in most full length PA sequences is found at or around residues 163-168, may be inactivated by deletion, insertion, or substitution within or near to the furin cleavage site. For example, all of the furin cleavage site residues of native PA may be deleted. Other mutant PAs include those in which the dipeptide Phe-Phe has been modified to render the PA resistant to chemotrypsin. A PA fragment or PA fusion protein may also be a PA mutant.

Specific examples of PA fragments include those in U.S. Pat. No. 7,201,912, for example, PA64 expressed by pBP111, PA47 expressed by pBP113, PA27 expressed by pBP115. Some of those fragments also include mutations to, for example, eliminate the furin cleavage site RKKR (SEQ ID NO: 2) or the chemotrypsin sensitive site formed by the dipeptide sequence Phe-Phe (FF). In addition, fragments may include one or two additional amino acids at the N-terminus. Examples of fusion proteins involving PA include those in U.S. Pat. No. 7,201,912, for example the PA-LF fusion proteins expressed by plasmids pBP107, pBP108, and pBP109. The invention also includes formulations comprising a HIS-tag PA. When a fragment, mutant, or fusion protein is used, however, it is generally desirable that the fragment, mutant, or fusion protein elicit protective immunity to a challenge with an $LD_{50}$ of anthrax spores of the Ames strain in one or more of mice, guinea pigs, or rabbits.

Although PA from a recombinant source is generally preferred, formulations prepared from non-recombinant sources can also be used and the stability of such preparations improved by the formulations of the invention.

Methods of expression *B. anthracis* proteins, including PA (as well as fragments, mutants, and fusion proteins), are known and include those described in U.S. Pat. No. 7,201,912, which is incorporated by reference in its entirety.

V. VACCINES

Formulations of the invention can be used to elicit antibodies to protective antigen, which may provide protection from infection with anthrax. Thus, one embodiment of the invention is a vaccine comprising one or more of the formulations comprising PA.

When the formulations are used as a vaccine, they typically, although not always, further comprise one or more adjuvants. Examples of adjuvants include, but are not limited to, aluminum (e.g., Alhydrogel), ImmunoStimulatory Sequences (ISS, CpG), and calcium phosphate. For aluminum hydroxide, the protein formulation is added to the adjuvant at the desired ratio (e.g., 175 μg PA per 1500 μg aluminum). In some embodiments, the vaccine comprises approximately 200 μg/mL rPA102 and approximately 0.5 mg/mL (for example, between 0.43 and 0.58 mg/mL) aluminum (e.g., Alhydrogel). In further embodiments, the vaccine comprises approximately 250 μg rPA per 250 to 100 μg aluminum (e.g., Alhydrogel). For ISS, protein samples are generally used at a final protein concentration 50 μg/ml. Other non-limiting examples of adjuvants include but are not limited to: CGP7909 (see U.S. Pat. No. 7,223,741, which is herein incorporated by reference in its entirety), N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Typically, vaccines are prepared as injectables, either as liquid solutions or suspensions. Of course, solid forms suitable for solution in, or suspension in, liquid prior to injection may also be prepared. The preparation may also be emulsified, or the peptide encapsulated in liposomes or microcapsules.

Vaccine administration is generally by conventional routes, for instance, intravenous, subcutaneous, intraperitoneal, or mucosal routes. The administration may be by parenteral injection, for example, a subcutaneous or intramuscular injection.

The vaccines are administered in a manner compatible with the dosage formulation, and in such amount as will be prophylactically and/or therapeutically effective. The quantity to be administered, which is generally in the range of 5 μg to 250 μg of antigen per dose, depends on the subject to be treated, capacity of the subject's immune system to synthesize antibodies, and the degree of protection desired. In one embodiment, the vaccine comprises at least about 10 μg PA, 25 μg PA, 50 μg PA, 75 μg PA, 100 μg PA, 125 μg PA, 150 μg PA, 200 μg PA, or 225 μg PA. Precise amounts of active ingredient required to be administered may depend on the judgment of the practitioner and may be particular to each subject.

The vaccine may be given in a single dose schedule, or optionally in a multiple dose schedule. The vaccine composition may be administered, for instance, in a 0.5 mL dose. For pre-exposure prophylaxis, a multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months.

For post-exposure prophylaxis, the vaccine may also be administered according to a multiple dose regimen. For instance, in one embodiment, the vaccine is administered in 3 doses at times 0, 2 and 4 weeks post exposure. The dosage regimen will also, at least in part, be determined by the need of the individual and be dependent upon the judgment of the practitioner.

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFN-beta, IFN-alpha).

In one embodiment, the vaccine is administered to a subject post-exposure to anthrax. In this embodiment, the vaccine may be administered in conjunction with an antibiotic. Antibiotics that may be administered with the vaccine include, but are not limited to, penicillin, doxycycline and ciprofloxacin.

The formulations of the invention may be further modified to provide other formulations that are suitable for other modes of administration include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The invention includes methods of treating (post-exposure prophylaxis) or preventing (pre-exposure prophylaxis) an anthrax infection comprising administering to a subject a pharmaceutically effective amount of a vaccine of the invention. In one embodiment, the anthrax infection is the result of inhaling anthrax (i.e., inhalation anthrax). As used herein, a pharmaceutically effective amount of a vaccine is an amount that induces an immune response. In one embodiment, a pharmaceutically effective amount of a vaccine is an amount comprising at least 25 μg PA. As used herein, a subject is a mammal such as a human.

The invention also provides methods of stimulating an immune response in a subject by administering the to subject an amount of a vaccine of the invention sufficient to stimulate an immune response. In some embodiments, immune stimulation is measured by an increased protective effect compared to a vaccine comprising, for instance, the same peptide in a buffer solution comprising 20 mM sodium phosphate/20 mM Tris/150 mM sodium chloride and 001% polysorbate 80, pH 7.4. In other embodiments, immune stimulation is measured by increases in antibody titer that is specific for the antigen in the vaccine. In still other embodiments, immune stimulation is measured by an increased frequency in cytotoxic T lymphocytes specific for the antigen in the vaccine.

The immunogenicity of the rPA formulations can be tested as described in the various examples. For example, mice can be immunized with, for example, 10 μg, 20 μg, or more of rPA suspended in an adjuvant emulsion. Control mice are immunized with saline emulsified in adjuvant for use as negative controls. The mice are generally immunized, then bled at various intervals, e.g., day 0, day 21 and day 28 post-immunization. The serum is then analyzed for the presence of specific antibody, e.g., by ELISA, which can also be used to determine the titer of the antisera.

A mouse toxin-neutralizing antibody assay can also be used to determine if the rPA formulations elicit protective antibodies. In this assay, mice immunized with rPA are then challenged i.p. with 2 lethal doses of lethal toxin (i.e., PA and lethal factor (LF)). Four days after challenge, the mice are scored for survivors.

The rPA formulations can also be used to prepare compositions comprising neutralizing antibodies that immunoreact with the anthrax toxin. The resulting antisera can be used for the manufacture of a medicament for treating exposure to anthrax. In one embodiment of the invention, the antibody composition comprises a purified anti-PA antibody. By "purified," it is meant that the antibody is substantially free of other biological material with which it is naturally associated. Purified antibodies of the invention are at least 60% weight pure, at least 70% weight pure, at least 80% weight pure, at least 90% weight pure or at least 95% weight pure. The antisera, or antibodies purified from the antisera, can also be used as diagnostic agents to detect either PA fragments or native protein.

The invention will be further clarified by the following examples, which are intended to be purely exemplary of the invention and in no way limiting.

VI. EXAMPLES

Example 1 rPA102 Drug Product and Stability Assays

Stability issues with the FDP formulations used in VaxGen's initial phase 2 clinical trial led to the material produced for clinical trial VAX023 being placed on clinical hold by the FDA. This resulted in a decision to further examine the degradation pathways for rPA102 and to re-evaluate alternative formulations for the rPA102 vaccine.

In order to properly evaluate the protein and understand the degradation pathways, several additional assays were developed. These assays included:

Native Elutability (NE) which was used to estimate the fraction of rPA102 which could be recovered from the Alhydrogel under non-denaturing conditions; results from the native elutability assay are reported as relative to the native elutability for each specific formulation at time=0. A decrease in NE is interpreted as due either to conformational changes in rPA102 or to deamidation, resulting in increased binding to the Alhydrogel.

rPA102 Biochemical Activity assay based on the macrophage lysis assay (MLA) is used as a functional cell based bioassay which measures the cytotoxicity of lethal toxin. Lethal toxin is formed by mixing lethal factor with either reference rPA or the test rPA. The assay requires the elution of active rPA102 from the Alhydrogel. A decrease in activity is interpreted as a change in the native conformation of the rPA eluted from the Alhydrogel.

Flow Cytometric Immunoassay (FCIA) is used to measure the exposure of different rPA102 epitopes. The FCIA assay is based on the binding of monoclonal antibodies to specific epitopes. The test antibodies include 14B7 that blocks rPA102 cell-receptor binding, which indicates rPA102 is in its native conformation. Antibody 15F7 has been shown to bind epitopes of unfolded rPA102, and therefore can detect non-native conformation. The assay is performed while the antigen is bound to the Alhydrogel. A decrease in the ratio of signal from the 14B7 antibody relative to signal from the 15F7 antibody is interpreted as a change in the native conformation of the rPA102.

Peptide map analysis by RP-HPLC/ESI-MS provides information on deamidation of the rPA102.

Front Faced Fluorescence (FFF) measures the intrinsic tryptophan fluorescence and provides information on protein tertiary structure changes. Changes in tryptophan exposure to the environment are interpreted as conformational changes of the rPA102, either free or bound to Alhydrogel.

These analytical methods were utilized in a series of experiments designed to generate a better understanding of the reasons for the loss of rPA102 potency in the initial phase 2 trial and to develop more stable formulations. Data from the FCIA assay (FIG. 1) demonstrated that rPA102 adsorbed to Alhydrogel undergoes conformational changes as a function of incubation time and incubation temperature. rPA102 in the native protein conformation (based on the availability of the 14B7 epitope) positively correlated with an increased ability to elute rPA102 from Alhydrogel under non-denaturing conditions. rPA102 in the non-native protein conformation (based on the availability of the 15F7 epitope) was found to have a negative correlation with the ability of rPA102 to be eluted from Alhydrogel under non-denaturing conditions. These data indicate that the FCIA method is capable of assessing rPA in its native conformation. These conclusions were confirmed by data generated during analysis using the NE and MLA assays. Data from the peptide map analysis indicated an increase in deamidation, potentially resulting in an increased negative charge that could lead to the formation of unusually strong bonds between the rPA102 molecule and the Alhydrogel.

Figure 2:
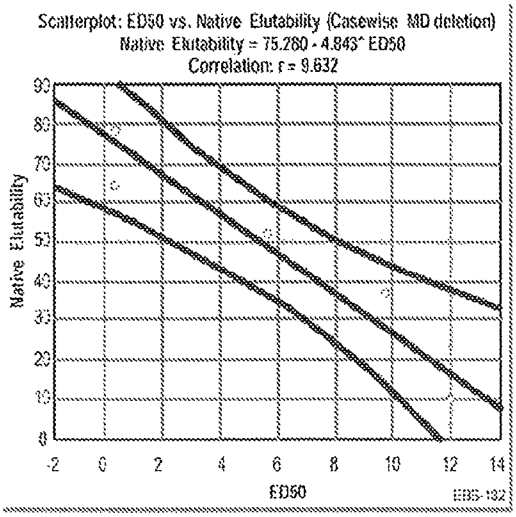
FIG. 2. A strong correlation exists between native elutability and the $ED_{50}$ generated by the rabbit ELISA.
Figure 3:
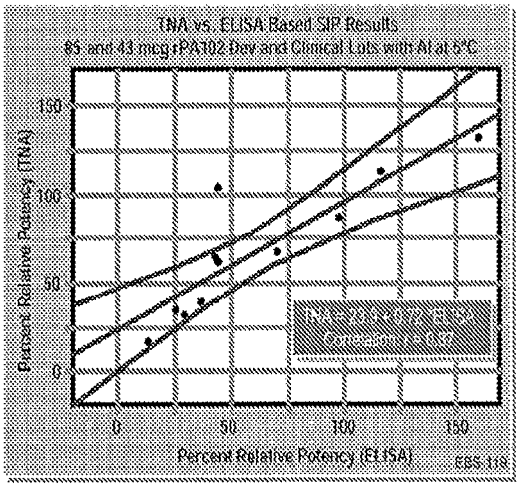
FIG. 3. Rabbit serum anti-PA IgG levels strongly correlated with TNA activity.

Further analysis of the data shows a strong statistical correlation ($P<0.05$) between the in vitro assays, such as the native elutability assay and the in vivo ELISA-based rabbit potency assay (FIG. 2). Other studies (data not shown) indicate that high immunogenicity (low $ED_{50}$) correlates with increased exposure of the epitope recognized by the 14B7 antibody, high native elutability, and low percent deamidation, all of which are markers of rPA102 in the native confirmation. A statistically significant correlation was also established for rPA102 protein activity as measured by MLA and the rabbit potency assay. In addition, a strong correlation was observed between the ELISA results and data from the TNA assay generated using rabbit sera (FIG. 3). These correlations provide further assurance of the relevance of results obtained using the biochemical/biophysical stability assays.

Figure 4:
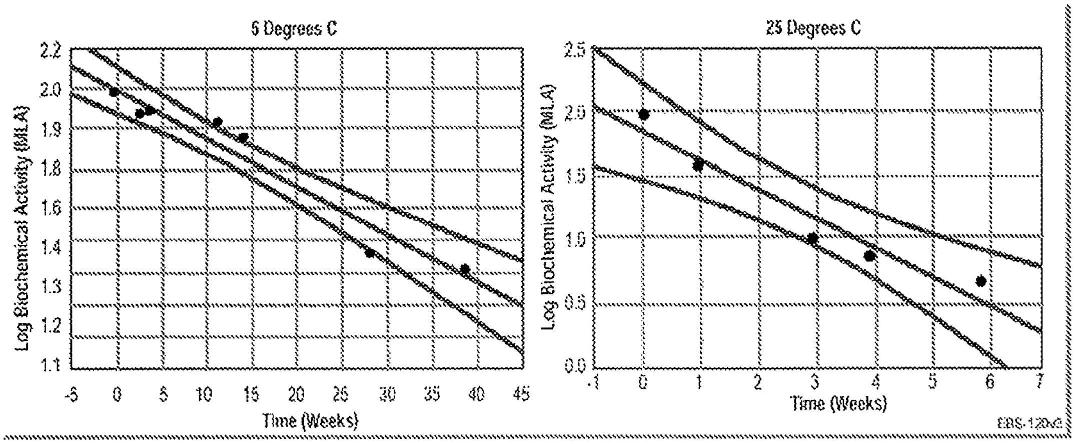
FIG. 4. Biochemical activity measurements (MLA assay) indicate that the protein in the phosphate spike formulation loses conformation and activity at a 10-fold greater rate at 25° C. relative to protein stored at 2-8° C.

Correlations were also established between degradation rates at 2-8° C. and at 25° C., based primarily on the extensive data from the phosphate spike formulation and the newly developed in vitro assays (FIG. 4). rPA102 stored at 25° C. and at 2-8° C. for up to 38 weeks was analyzed for the loss of biochemical activity using the MLA assay. The data presented demonstrates both the linear nature of the loss of rPA102 biochemical activity over time and the different rates of protein degradation for the two temperatures. Based on this analysis, phosphate spike stability results for one week at 25° C. correspond to approximately 3 weeks at 2-8° C. Results from the other assays support these conclusions.

Example 2

Formulation Development: Physico-Chemical Studies

A second series of formulation studies was carried out which was more focused on the addition of excipients to the formulation buffer including: glycine; alanine and proline; polysorbates and other sugars; salts as well as variations in final pH. The experiments were carried out using a statistical "design of experiments" screening approach to evaluate both the individual and combined effects of the various excipients. The results indicated that proline (Pro), glycine (Gly) and alanine (Ala)-based formulation buffers had a stabilizing effect on rPA bound to Alhydrogel. An experiment was then performed to identify the optimum excipient concentrations and pH in order to obtain maximum protein stability. Based on the model simulations the following promising formulation prototypes were identified:

Gly formulation: 250 mM Gly, 25 mM Na Phosphate buffer, 0.01% PS80, pH 7.0.

Ala formulation: 220 mM Ala, 25 mM Na Phosphate buffer, 0.01% PS80, pH 7.0.

Pro formulation: 150 mM Pro and 100 mM NaCl, 25 mM Na Phosphate buffer, 0.01% PS80, pH 7.4.

Figure 5:
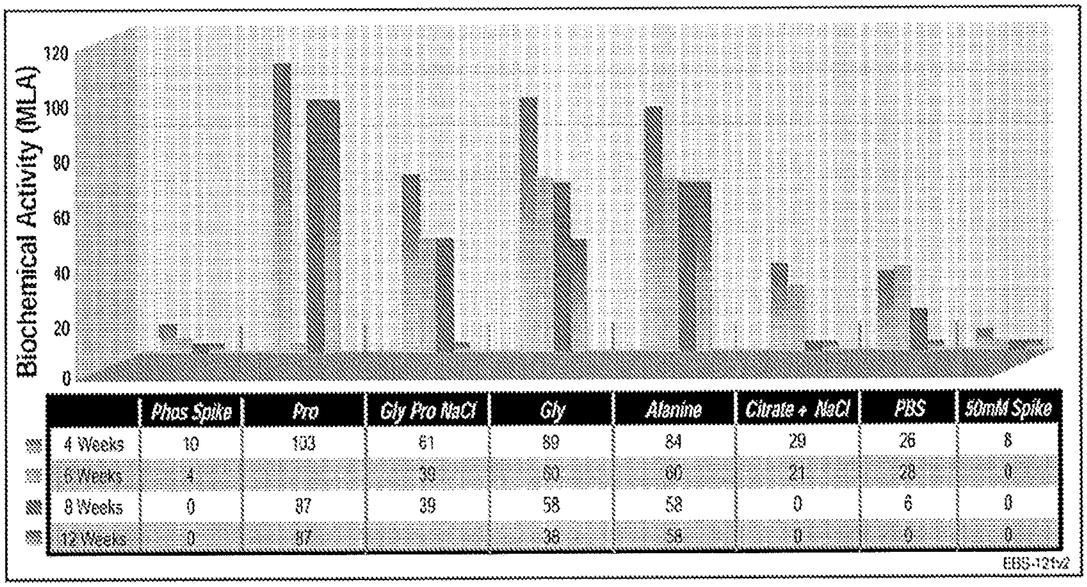
FIG. 5. The new formulations demonstrated improved stability at 25° C. based on results from the MLA assay.

Pro/Gly formulation: 50 mM Gly, 100 mM Pro, 100 mM NaCl, 25 mM Na Phosphate buffer, 0.01% PS80, pH 7.4.

rPA102 was formulated using the four new formulation buffers at a protein to Alhydrogel ratio of 175 μg rPA102 per 1500 μg aluminum (85 μg rPA and 750 μg aluminum (Alhydrogel) per 0.5 mL dose). Other formulations are also possible, for example, those comprising approximately 200 μg/mL rPA102 and approximately 0.5 mg/mL aluminum. Phosphate spike Alhydrogel, previously determined by VaxGen to be more stable than the formulations used in the phase 1 and phase 2 studies, was used as a control. The phosphate spike formulation contains 20 mM sodium phosphate/20 mM Tris/150 mM sodium chloride and 0.01% PS80, pH 7.4. These formulations were placed on stability at 25° C. for 3 months. The stability of the formulation prototypes were evaluated using the assays selected to determine the degradation pathways. The results from the stability studies were reproducible and indicate significant improvement in FDP stability compared to the phosphate spike formulation. Improvements in stability of the rPA102 included:

Prototype formulations containing proline or alanine had recoverable levels of rPA102 after 12 weeks incubation at 25° C. which were similar to the level of recoverable rPA102 at time=0. Recoverable rPA102 levels from the phosphate spike formulation were 20% of the time=0 value The biochemical activity of rPA102 after 12 weeks, as measured by MLA, for the proline-based formulation was 84%; while after 12 weeks incubation at 25° C. formulations containing alanine and glycine (See FIG. 5) retained 80% and 60% MLA activity, respectively. At the same time the phosphate spike formulation had ~40% rPA102 biochemical activity after only 1-week at 25° C. and after 4 weeks had decreased to <10% rPA102 biochemical activity. Data from this assay was also reported as a percentage relative to a time equals zero sample.

Figure 6:
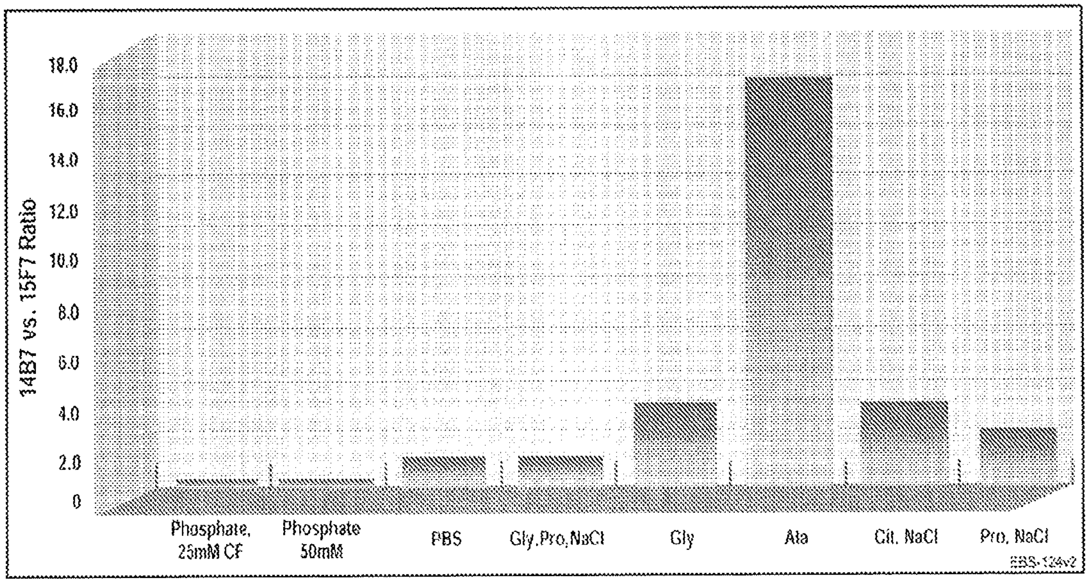
FIG. 6. The new formulations demonstrated improved stability at 25° C. based on the relative availability of neutralizing vs. non-neutralizing epitopes using the FICA assay.

FCIA analysis of the phosphate spike formulation shows significant level of rPA unfolding after one month incubation at 25° C. as measured by epitope exposure (See FIG. 6). The extent of rPA unfolding observed in formulation prototypes Ala, Pro or Gly is substantially lower indicating that the rPA configuration was closer to the native structure.

Peptide map analysis by RP-HPLC/ESI-MS indicates significant decrease of the level of deamidation in the formulation prototype containing Ala after 3 months incubation at 25° C., while the phosphate spike formulation is almost completely deamidated.

These data, combined with the temperature correlations described earlier, indicate that the projected real time stability of the alanine based formulation at 2-8° C. should be at least two years.

The preliminary data supported further investigation of three formulations: the alanine-based formulation; the proline-based formulation and the glycine-based formulation. While results varied from assay to assay, the alanine-based formulation was consistently stable across all assays while the proline and glycine-based formulations had a higher degree of variation in stability from assay to assay.

We have continued formulation development by conducting a series of physichochemical and animal studies to select the best formulation to take rPA102 to licensure. rPA102 was formulated using the alanine, proline, glycine, and phosphate spike formulations and compared to material produced using the same formulations at VaxGen in July 2007. All samples were stored at 2-8° C. The phosphate spike formulation was included to correlate results from earlier studies.

Figure 7:
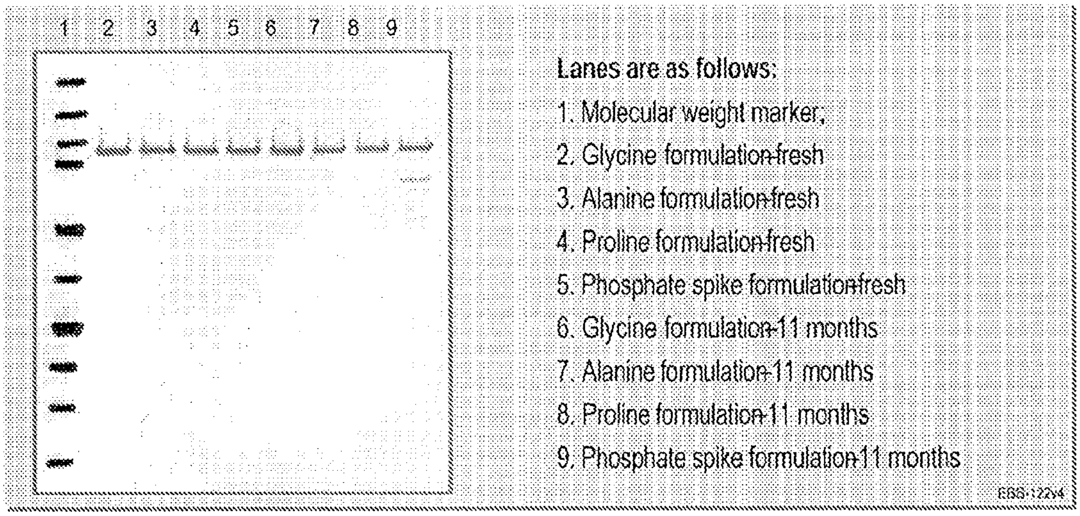
FIG. 7. The rPA102 formulated using the new formulations demonstrate increased stability relative to the phosphate spiked formulation. The figure is a western blot using anti-rPA as the primary antibody.
Figure 8:
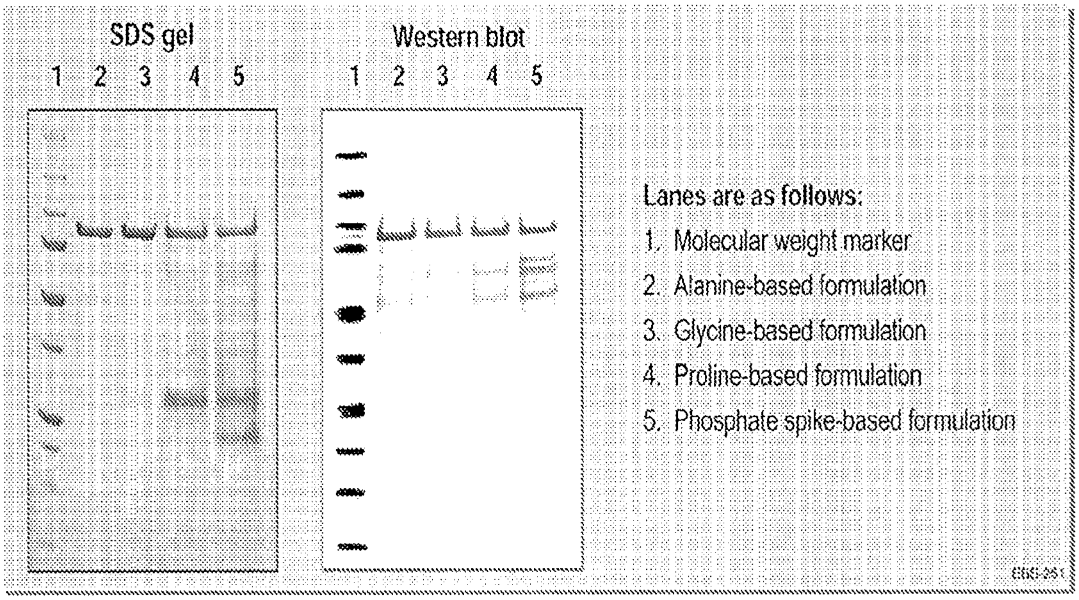
FIG. 8. rPA102 in the proline and phosphate spike formulations and stored at 25° C. had substantially more degradation than rPA in the alanine- and glycine-based formulations.
Figures 9, 10:
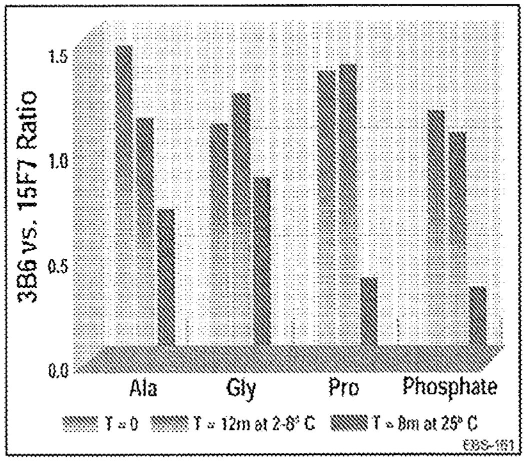
FIG. 9. Results from the MLA assay indicate that rPA102 is most stable in the alanine and glycine formulations and least stable in the proline and phosphate spike formulations. All percentages are normalized to an rPA reference standard.
FIG. 10. While the alanine and glycine based formulations have the highest 3B6 to 15F7 ratio at 25° C., all four formulations are similar when stored at 2-8° C. for 12 months.

Results from degradation analysis using western blot indicate that the rPA102 in the alanine and glycine formulations stored for 11 months at 2-8° C. were intact whereas the proline and phosphate-spike formulations had degradation resulting in peptide backbone breakage (FIG. 7). rPA102 in the amino acid formulations stored at 25° C. for 7 months and analyzed by SDS-PAGE and western blot had similar degradation patterns to those seen for samples stored at 2-8° C. (FIG. 8). However, the level of protein degradation was substantially lower than that seen at 25° C.

rPA102, eluted from Alhydrogel under non-denaturing conditions showed similar results with the lowest relative rPA102 activity being the 11 month phosphate spike and proline formulations. The highest MLA activity was seen in the freshly prepared glycine and alanine formulations as shown in FIG. 9. All MLA activity assay values were compared to an rPA reference standard.

rPA102 was also shown to retain the native conformation based on the relative abilities of the antibodies 3B6 and 15F7 to bind to the rPA102 (FIG. 10). 3B6 is a replacement for 14B7, which was no longer available. However; 3B6 binds to the same neutralizing epitope as 14B7 and provides similar data on the relative availability of the neutralizing epitope. 3B6 mAb binds to exposed epitope in native rPA and 15F7 binds only to the unfolded rPA102. Each mAB is conjugated to a different fluorescent dye. FCIA assays measure binding of each mAB to rPA102. The alanine-containing and glycine-containing formulations retained the highest overall level of native rPA102 protein conformation compared to the phosphate spike and proline-based formulations after storage for 8 months at 25° C.

Figure 11:
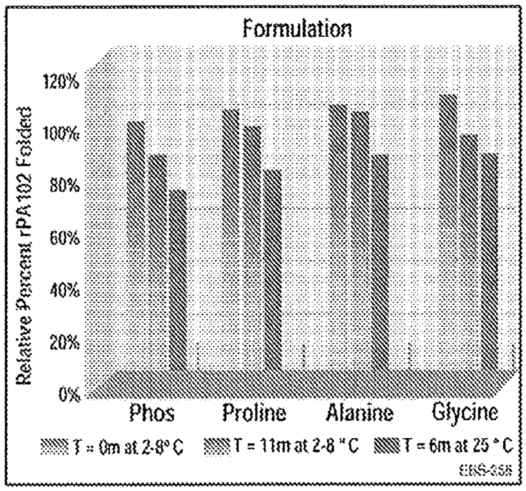
FIG. 11. The Alanine-based formulation retains the highest overall level of protein folding for the formulations tested.

Results from the front faced fluorescence assay that measures fluorescence of exposed Trp residues (normally buried inside the protein hydrophobic pockets) confirm that the alanine-based formulation retained the highest overall level of native rPA102 protein conformation as compared to the phosphate spike, the proline, and the glycine-based formulations after storage for 11 months at 2-8° C. (FIG. 11).

Example 3

Preliminary Potency and Stability Studies

Figure 12:
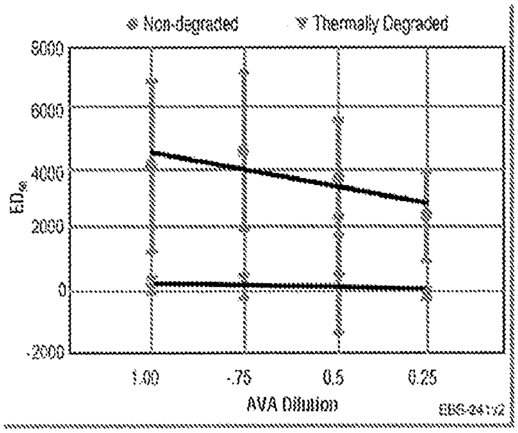
FIG. 12. AVA incubated at 48-55° C. for 5 days (thermally degraded) has substantially lower levels of potency compared to AVA stored under normal conditions of 2-8° C.

The stability and potency of the revised rPA102 formulations were tested utilizing a mouse toxin-neutralizing antibody assay (TNA assay) currently under development at Emergent. This assay uses mice immunized with formulated rPA. Sera from the mice are then tested both by ELISA and by the TNA assay. The TNA assay correlates to protection in animal challenge studies (Pitt et al., 2001). In addition, preliminary data generated from BioThrax stability studies indicates that the mouse TNA assay detects differences between non-degraded and thermally degraded AVA (FIG. 12 on the next page). Antibody titers are measured using a standard rPA-binding ELISA.

Two lots (fresh and aged 11 months) of each three rPA102 formulations were administered to mice: 1) proline; 2) alanine; and 3) glycine. CD-1 female mice (210), 6-8 weeks old and 20-25 g body weight were used for the study. Mice were bled prior to vaccination to determine pre-immune titers; post-vaccination bleeds were performed on days 21 and 28. The rPA102 vaccine was administered IP on day 0 of the study at dilutions of 1/4 [21.25 μg rPA102 and Alhydrogel (187.5 μg aluminum) per dose] (FIG. 13) and 1/8 [8.82 μg rPA102 and Alhydrogel (93.8 μg aluminum) per dose] (FIG. 14). AVA at dilutions of 1/2 and 1/4 was used as a positive control. The study design for each experiment is summarized in FIG. 13 and EBS 14.

Sera from the pre-inoculation and from days 21 and 28 post immunization were analyzed utilizing the TNA assay and the anti-PA IgG ELISA. TNA results are presented as $ED_{50}$ and anti-PA IgG values from the ELISA are expressed as μg/mL relative to an external reference standard.

Figure 15:
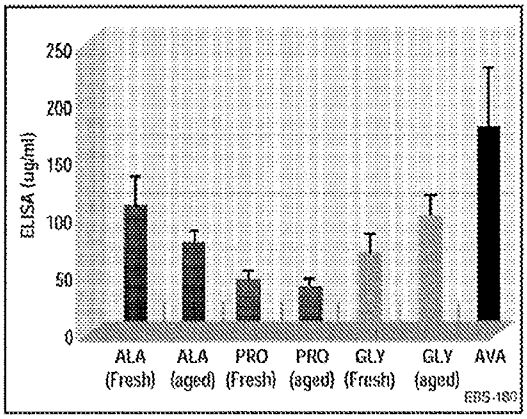
FIG. 15. Anti-PA IgG concentrations after rPA102 immunization (1/4 dilution) with fresh and aged vaccines in mouse sera. Anti-PA IgG concentrations after rPA102 immunization (1/8 dilution) with fresh and aged vaccines in mouse sera.
Figure 16:
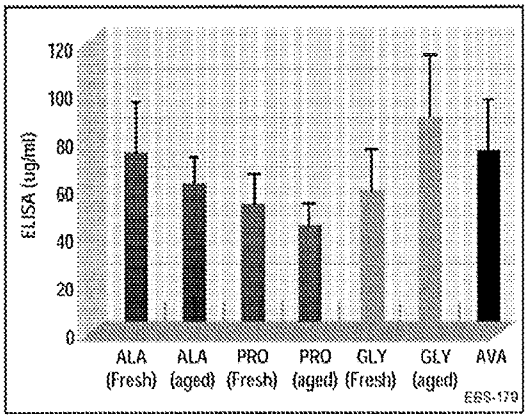
FIG. 16. Anti-PA IgG concentrations after rPA102 immunization (1/8 dilution) with fresh and aged vaccines in mouse sera.

All three rPA102 vaccine formulations induced robust immune responses at both dilutions. There was no statistical difference (P>0.05) in levels of anti-rPA102 IgG between the freshly prepared vaccines and vaccines stored at 2-8° C. for 11 months (FIGS. 15 and 16). The alanine- and glycine-based formulations induced slightly higher levels of anti-PA IgG than the proline-based formulation; however, these differences were not statistically significant.

Figure 17:
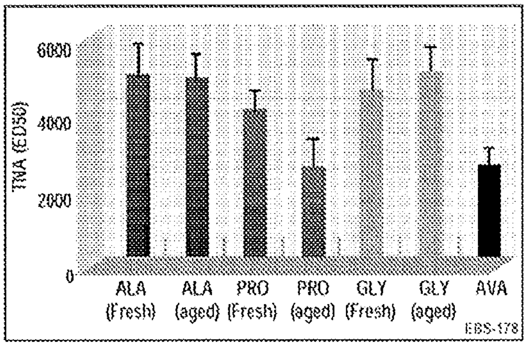
FIG. 17. TNA ($ED_{50}$) titers after rPA102 immunization (1/4 dilution) with fresh and aged vaccines in mouse sera.
Figure 18:
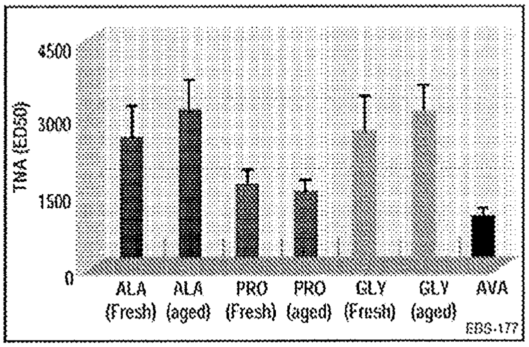
FIG. 18. TNA ($ED_{50}$) titers after rPA102 immunization (1/8 dilution) with fresh and aged vaccines in mouse sera.

Results from the TNA assay were consistent with the ELISA results. The TNA assay demonstrated production of functionally active, anti-PA neutralizing antibodies in response to rPA102 vaccination (FIGS. 17 and 18). Sera from mice injected with the aged rPA formulations demonstrated no difference in toxin neutralizing activity relative to mice injected with the freshly prepared rPA. Sera from animals injected with the alanine- or glycine-based formulations had higher TNA titers than sera from animals inoculated with the proline based formulation (P<0.05). There was no statistical difference between TNA titers induced by the alanine- and glycine-based formulations.

Figure 19:
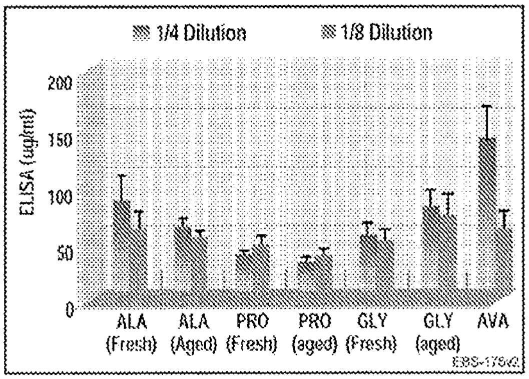
FIG. 19. Anti-PA IgG concentrations after rPA102 immunization (1/4 and 1/8 dilutions) with fresh and aged vaccines in mouse sera.

Anti-PA IgG concentrations did not vary significantly over the two dose levels (1/4 and 1/8) for any rPA formulations tested (FIG. 19). But the two dose levels for AVA (1/2 and 1/4) did produce a dose dependent IgG response indicating that the assay was operating properly and was in the linear range for AVA (FIG. 19).

Figures 20, 21:
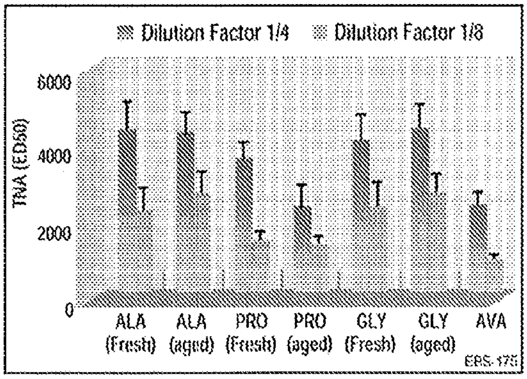
FIG. 20. TNA (ED50) titers after rPA102 immunization (1/4 and 1/8 dilutions) with fresh and aged vaccines in mouse sera collected on day 21.
FIG. 21. Formulations to be tested for anti-microbial effectiveness.

Results from the TNA assay demonstrated a dose-dependent effect for the vaccine (FIG. 20). Although the dilution effect was present for both the fresh and the aged rPA formulations, there was no apparent decrease in rPA induced neutralizing activity over time. The immunological data obtained from day 28 sera confirmed the day 21 sera results.

Data from the mouse TNA assay demonstrate that all rPA102 vaccine formulations induce toxin neutralizing antibodies in the mouse model. In addition, all three formulations are stable over 11 months at 2-8° C. in that there was no decrease in potency of the formulated rPA102. No statistically significant difference in immunogenicity of the rPA102 vaccine in the alanine-based formulation was observed after storage for 18 months at 2-8° C. (data not shown). Finally, both the alanine and glycine-based formulations generate more toxin neutralizing antibodies than the proline-based formulation.

While the data from the physicochemical assays showed varying levels of protein activity, native conformation and availability in the different formulations; when the results were viewed as a whole, the alanine-based formulation is the most stable and presents the highest combination of desired characteristics. These data are supported by the results from the mouse ELISA and TNA assay.

Example 4

Immunogenicity and Efficacy of rPA102 Vaccine Candidate Formulations in Guinea Pigs The immunogenicity and efficacy of the alanine-, proline- and glycine-containing formulations of rPA102 vaccine were evaluated in a guinea pig lethal anthrax challenge model. Sixty-four guinea pigs were randomly assigned to 8 groups of 8 animals (equal number of males and females per group). rPA102 vaccine formulations containing the glycine, alanine and proline formulation buffers as described in example 2 were evaluated. Vaccine formulations contained 100 μg rPA102 and Alhydrogel (750 μg aluminum) per 0.5 mL dose. The source of the rPA102 was cGMP BDS lot AN0030. Groups of guinea pigs were vaccinated once (on day 0) or twice (on days 0 and 12) subcutaneously (SC) with 0.5 mL of the appropriate rPA102 vaccine formulation or with undiluted BioThrax® anthrax vaccine adsorbed as a positive control. On day 30, animals were challenged via the intradermal (ID) route with 200 $LD_{50}$ of anthrax spores and observed for mortality for 10 days post-challenge. Serum samples were collected prior to the first vaccination and on day 28, and the immune response was evaluated using TNA and anti-PA IgG ELISA.

Figure 24:
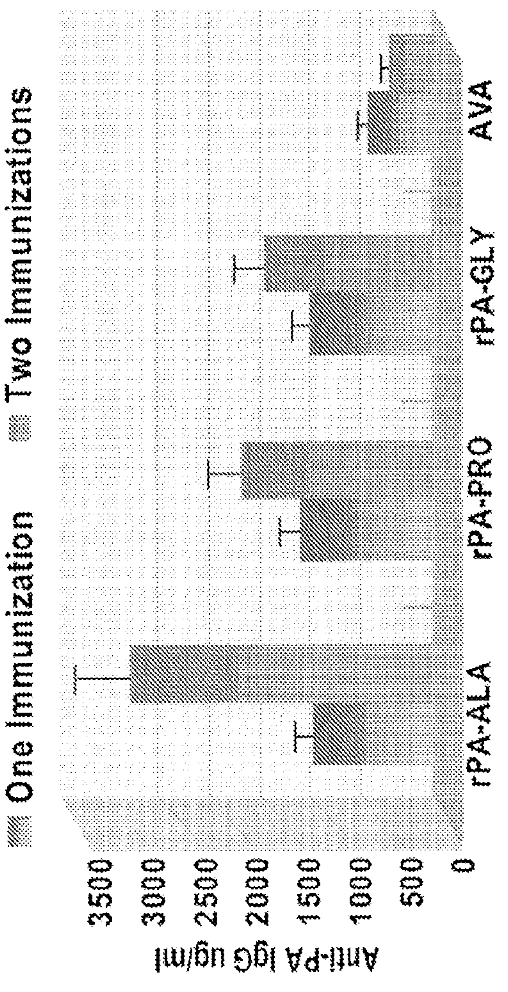
FIG. 24. Anti-PA IgG concentrations in guinea pig sera after immunization with rPA102 vaccine candidates.
Figure 25:
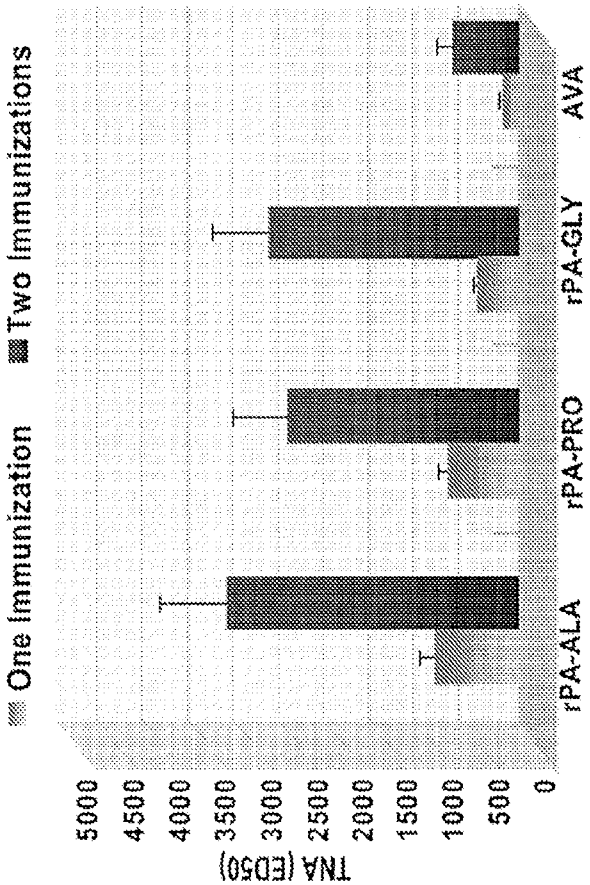
FIG. 25. TNA titers in guinea pig sera after two immunizations with rPA102 vaccine candidates.

Most rPA102 vaccine-immunized animals survived the anthrax challenge except for one group in the Group 2 that was immunized with a single dose of the proline-formulated vaccine. The highest mortality rate (37.5%) was observed in Group 4 vaccinated with a single dose of BioThrax where 3 animals died. All three rPA formulations induced a robust humoral immune response, even after a single immunization, as measured by anti-PA IgG ELISA and TNA. The second immunization induced a substantial increase in both anti-PA IgG and neutralizing antibody levels. The results are illustrated in FIGS. 24 and 25.

TABLE 1

Guinea Pig Survival after Immunization with rPA102 Vaccine Candidates or BioThrax

| Group Number | Vaccine | Vaccination Schedule (Days) | No. Alive/No. Dosed (%) |
|---|---|---|---|
| 1 | rPA102-ALA | 0 | 8/8 |
| 2 | rPA102-PRO | 0 | 6/7[a] |
| 3 | rPA102-GLY | 0 | 8/8 |

TABLE 1-continued

| Guinea Pig Survival after Immunization with rPA102 Vaccine Candidates or BioThrax | | | |
|---|---|---|---|
| Group Number | Vaccine | Vaccination Schedule (Days) | No. Alive/No. Dosed (%) |
| 4 | BioThrax | 0 | 5/8 |
| 5 | rPA102-ALA | 0, 12 | 7/7[a] |
| 6 | rPA102-PRO | 0, 12 | 8/8 |
| 7 | rPA102-GLY | 0, 12 | 8/8 |
| 8 | BioThrax | 0, 12 | 8/8 |

[a]One animal in each of Group 2 and Group 5 died prior to the initiation of the study.

Example 5

Immunogenicity and Efficacy of rPA102 Vaccine Candidate Formulations in Rabbits The immunogenicity and efficacy of the rPA102 vaccine candidate formulations were also evaluated in the New Zealand White (NZW) rabbit lethal aerosol *B. anthracis* spore challenge model.

Forty-eight NZW rabbits were randomly assigned to 6 groups of 8 animals (equal number of males and females per group). Animals were immunized on days 0 and 14 with different rPA102 formulations and BioThrax, as a positive control. Four rPA102 vaccine formulations, prepared in alanine (rPA-ALA), proline (rPA-PRO), glycine (rPA-GLY), or phosphate spike buffer (rPA102-Pi) were used. Each formulation was administered at 1:4 dilution of formulation that contained 100 μg rPA102/Alhydrogel with 750 μg aluminum per 0.5 mL dose. BioThrax was also diluted 1:4 prior to administration. A negative control group of animals was administered the Alhydrogel adjuvant only. Animals were challenged with 200 $LD_{50}$ of aerosolized *B. anthracis* spores (Ames strain; $LD_{50}$ of $1.05\times10^5$ CFU) on day 28, and observed for mortality for 14 days. Serum samples were collected prior to the first immunization and on day 27. Immune response was assessed by anti-PA IgG ELISA and TNA. The study design is outlined in Table 2.

TABLE 2

| Design of Rabbit Immunogenicity and Efficacy Study | | | | | |
|---|---|---|---|---|---|
| Group Number | No. of Animals | Vaccine | Vaccination Schedule (Days) | Aerosol Anthrax Challenge (Day) | Blood Collection Schedule (Days) |
| 1 | 8 | rPA102-ALA | 0, 14 | 28 | −4, 27 |
| 2 | 8 | rPA102-PRO | 0, 14 | 28 | −4, 27 |
| 3 | 8 | rPA102-GLY | 0, 14 | 28 | −4, 27 |
| 4 | 8 | BioThrax | 0, 14 | 28 | −4, 27 |
| 5 | 8 | rPA102-Pi | 0, 14 | 28 | −4, 27 |
| 6 | 8 | Alhydrogel | 0, 14 | 28 | −4, 27 |

Figure 26:
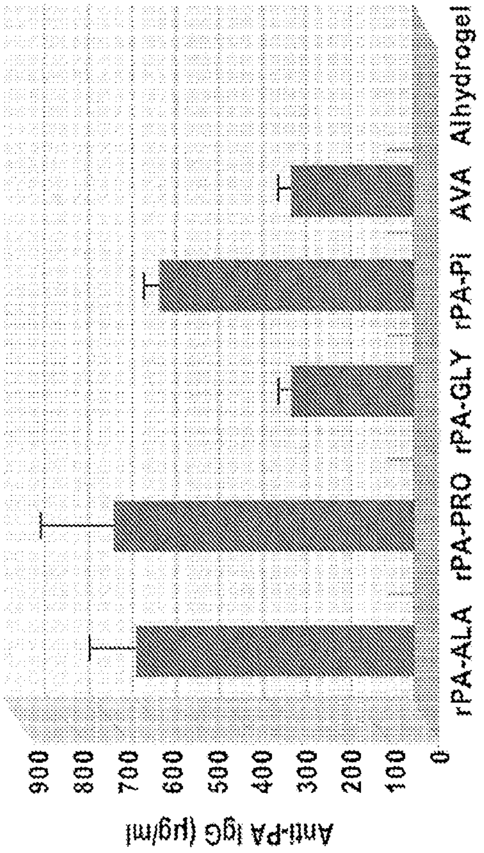
FIG. 26. Anti-PA IgG concentrations in rabbit sera after two immunizations with rPA102 vaccine candidates.
Figure 27:
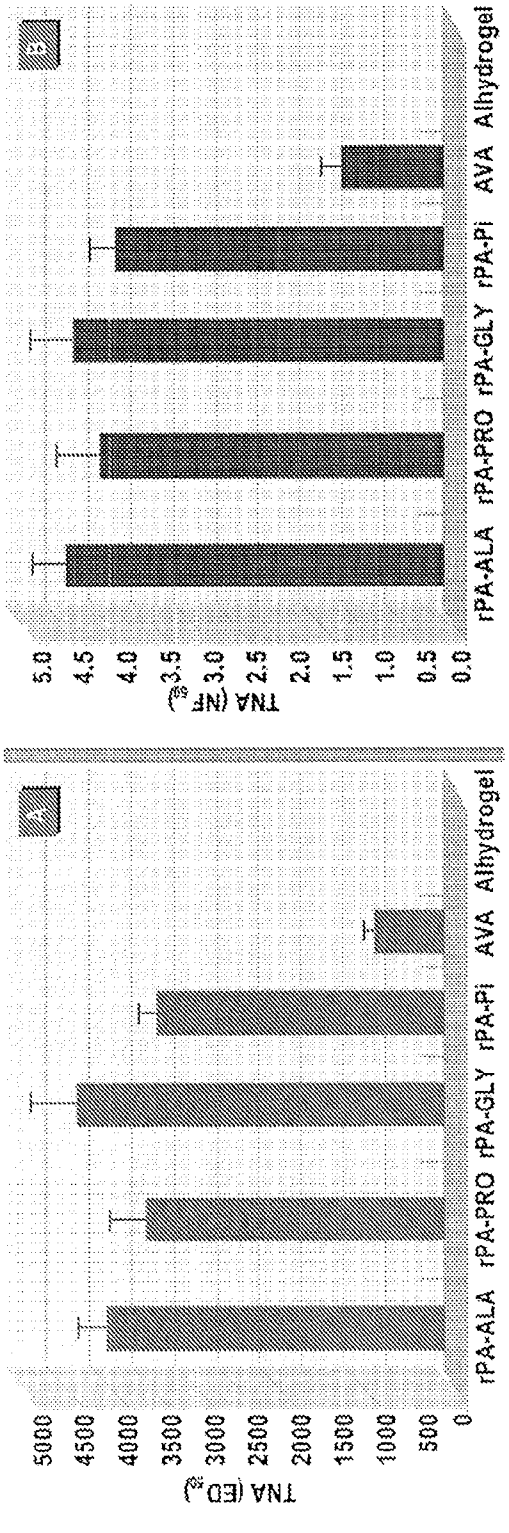
FIGS. 27A and 27B. TNA titers of rabbit sera after two immunizations with rPA102 vaccine candidates or BioThrax.

All animals that were immunized with rPA102-ALA, rPA102-PRO, rPA102-GLY, rPA102-Pi or BioThrax survived following lethal aerosol challenge with *B. anthracis* spores, while all animals in the adjuvant-only immunized group died (data not shown). All four rPA102 formulations induced a robust humoral immune response, as measured by anti-PA IgG ELISA and TNA assay (FIGS. 26 and 27). These results are consistent with those observed in the above-described guinea pig immunogenicity and efficacy study (Example 4), and demonstrate that all four rPA102 formulations are both immunogenic and protective against lethal challenge in the rabbit model.

Example 6

Evaluation of Various rPA102 and Alhydrogel Concentrations with Alanine

Following the identification of alanine as the most effective stabilizing excipient, rPA102 compositions comprising varying concentrations of rPA and Alhydrogel were evaluated. Specifically, this study evaluated rPA102 vaccine formulations (formulated with 20 mM Tris/0.9% NaCl (w/v), with 0.01% PS80 (w/v), pH 7.4) with the amounts of rPA102 and Alhydrogel as provided in Table 3 in an alanine buffer (220 mM alanine, 25 mM sodium phosphate buffer, 0.01% PS80 (w/v), at pH 7.0), at both 2-8° C., and 25° C.

TABLE 3

| Tested rPA102 and aluminum amounts | |
|---|---|
| Amt. rPA102 | Amt. Aluminum |
| 100 μg rPA102 | 750 μg Aluminum |
| 75 μg rPA102 | 750 μg Aluminum |
| 50 μg rPA102 | 750 μg Aluminum |
| 25 μg rPA102 | 750 μg Aluminum |
| 100 μg rPA102 | 250 μg Aluminum |
| 50 μg rPA102 | 250 μg Aluminum |
| 25 μg rPA102 | 250 μg Aluminum |

The formulations were tested for appearance (visual), free rPA102 (ELISA; expressed in μg/mL and in % (w/v)), pH, relative potency (mouse relative potency assay) and front faced fluorescence (expressed as relative percent of rPA102 folded.

The available results of this ongoing study are presented in Tables 4-7.

TABLE 4

| Stability results for the Screening Study of rPA102 Formulations with 750 μg aluminum (2-8° C.) | | | | |
|---|---|---|---|---|
| Test | 100 μg rPA102/ 750 μg Al | 75 μg rPA102/ 750 μg Al | 50 μg rPA102/ 750 μg Al | 25 μg rPA102/ 750 μg Al |
| Results, t = 0 | | | | |
| Appearance | White suspension | White suspension | White suspension | White suspension |
| Free rPA102, μg/mL (%)*** | 9.6 (9.6) | 7 (9.3) | 2.7 (5.4) | 0.9 (3.6) |
| pH | 6.95 | 7.02 | 6.95 | 7 |
| Relative Potency (mouse relative potency test) | 2.97 | 2.43 | 2.24 | 2.07 |
| FFF (%) | 96.6 | 108.4 | 96.6 | 114.2 |
| Results (2-8° C.), t = 1 month | | | | |
| Appearance | White suspension | White suspension | White suspension | White suspension |
| Free rPA102, μg/mL (%)*** | 4.8 (4.8) | 7.6 (10.1) | 1.4 (2.8) | 1.1 (4.4) |
| pH | 6.96 | 7.05 | 6.98 | 7.04 |
| Relative Potency (mouse relative potency test) | 3.02 | 2.19 | 3.02 | 1.70 |
| FFF (%) | 104.9 | 109 | 107.6 | 116.4 |
| Results (2-8° C.), t = 3 months | | | | |
| Appearance | White suspension | White suspension | White suspension | White suspension |
| Free rPA102, μg/mL (%)*** | 10 (10) | 9.8 (13) | 3 (6) | 1.2 (4.8) |
| pH | 7.1 | 6.92 | 7.06 | 6.95 |

TABLE 4-continued

Stability results for the Screening Study of rPA102 Formulations with 750 μg aluminum (2-8° C.)

| Test | 100 μg rPA102/ 750 μg Al | 75 μg rPA102/ 750 μg Al | 50 μg rPA102/ 750 μg Al | 25 μg rPA102/ 750 μg Al |
|---|---|---|---|---|
| Relative Potency (mouse relative potency test) | 2.38 | 1.61 | 2.28 | 1.44 |
| FFF (%) | 106.9 | 106 | 110.5 | 112 |
| Results (2-8° C.), t = 6 months | | | | |
| Appearance | White suspension | * | White suspension | * |
| Free rPA102, μg/mL (%)*** | 10 (10) | * | 4 (8) | * |
| pH | 7.03 | * | 7.02 | * |
| Relative Potency (mouse relative potency test) | * | ** | 1.57 | ** |
| FFF (%) | 107 | * | 103 | * |

* = Not Performed at this Time Point

** = Results Not Available

***= Percentage free rPA is a function of the concentration of the unbound rPA divided by the concentration of rPA formulated with Alhydrogel

TABLE 5

Stability Results for the Screening Study of rPA102 Formulations with 250 μg aluminum (2-8° C.)

| Test | 100 μg rPA102/ 250 μg Al | 50 μg rPA102/ 250 μg Al | 25 μg rPA102/ 250 μg Al |
|---|---|---|---|
| Results, t = 0 | | | |
| Appearance | White suspension | White suspension | White suspension |
| Free rPA102, μg/mL (%)*** | 56 (56) | 18 (36) | 4 (16) |
| pH | 6.86 | 6.92 | 6.96 |
| Relative Potency (mouse relative potency test) | 2.09 | 1.47 | 1.11 |
| FFF (%) | 96.6 | 96.6 | 109.4 |
| Results (2-8° C.), t = 1 month | | | |
| Appearance | White suspension | White suspension | White suspension |
| Free rPA102, μg/mL (%)*** | 30.4 (30) | 8.1 (16) | 4.4 (17) |
| pH | 6.87 | 6.89 | 7.03 |
| Relative Potency (mouse relative potency test) | 1.50 | 1.66 | 1.56 |
| FFF (%) | 102.4 | 102.4 | 109 |
| Results (2-8° C.), t = 3 months | | | |
| Appearance | White suspension | White suspension | White suspension |
| Free rPA102, μg/mL (%)*** | 42 (42) | 13 (26) | 4.9 (19.6) |
| pH | 7.04 | 7.02 | 7.0 |
| Relative Potency (mouse relative potency test) | 2.23 | 1.75 | * |
| FFF (%) | 104 | 104.8 | 107 |

TABLE 5-continued

Stability Results for the Screening Study of rPA102 Formulations with 250 μg aluminum (2-8° C.)

| Test | 100 μg rPA102/ 250 μg Al | 50 μg rPA102/ 250 μg Al | 25 μg rPA102/ 250 μg Al |
|---|---|---|---|
| Results (2-8° C.), t = 6 months | | | |
| Appearance | White suspension | White suspension | * |
| Free rPA102, μg/mL (%)*** | 57 (57) | 14 (28) | * |
| pH | 6.92 | 6.96 | * |
| Relative Potency (mouse relative potency test) | * | * | ** |
| FFF (%) | 102 | 103 | * |

* = Not Performed at this Time Point

** = Results Not Available

***= Percentage free rPA is a function of the concentration of the unbound rPA divided by the concentration of rPA formulated with Alhydrogel

TABLE 6

Stability results for the Screening Study of rPA102 Formulations with 750 μg aluminum (25° C.)

| Test | 100 μg rPA102/ 750 μg Al | 75 μg rPA102/ 750 μg Al | 50 μg rPA102/ 750 μg Al | 25 μg rPA102/ 750 μg Al |
|---|---|---|---|---|
| Results, t = 0 | | | | |
| Appearance | White suspension | White suspension | White suspension | White suspension |
| Free rPA102, μg/mL (%)*** | 9.6 (9.6) | 7 (9.3) | 2.7 (5.4) | 0.9 (3.6) |
| pH | 6.95 | 7.02 | 6.95 | 7 |
| Relative Potency (mouse relative potency test) | 2.97 | 2.43 | 2.24 | 2.07 |
| FFF (%) | 96.6 | 108.4 | 96.6 | 114.2 |
| Results (25° C.), t = 1 month | | | | |
| Appearance | White suspension | White suspension | White suspension | White suspension |
| Free rPA102, μg/mL (%)*** | 4.6 (4.6) | 7.5 (10) | 1.5 (3) | 1.1 (4.4) |
| pH | 7.02 | 7.04 | 7.01 | 7.02 |
| Relative Potency (mouse relative potency test) | 2.30 | 2.20 | 2.11 | 1.78 |
| FFF (%) | 95.5 | 100 | 95.5 | 109 |
| Results (25° C.), t = 3 months | | | | |
| Appearance | White suspension | White suspension | White suspension | White suspension |
| Free rPA102, μg/mL (%)*** | 7 (7) | 7.6 (10) | 3.5 (7) | 1.1 (4.4) |
| pH | 7.1 | 7.02 | 7.09 | 7.08 |
| Relative Potency (mouse relative potency test) | 1.30 | 0.99 | 1.88 | 0.98 |
| FFF (%) | 90 | 90 | 94.6 | 99.6 |
| Results (25° C.), t = 6 months | | | | |
| Appearance | * | * | * | * |
| Free rPA102, μg/mL (%)*** | * | * | * | * |
| pH | * | * | * | * |

TABLE 6-continued

| Stability results for the Screening Study of rPA102 Formulations with 750 μg aluminum (25° C.) | | | | |
|---|---|---|---|---|
| Test | 100 μg rPA102/ 750 μg Al | 75 μg rPA102/ 750 μg Al | 50 μg rPA102/ 750 μg Al | 25 μg rPA102/ 750 μg Al |
| Relative Potency (mouse relative potency test) | * | ** | 1.15 | * |
| FFF (%) | * | * | * | * |

* = Not Performed at this Time Point

** = Results Not Available

***= Percentage free rPA is a function of the concentration of the unbound rPA divided by the concentration of rPA formulated with Alhydrogel

TABLE 7

| Stability Results for the Screening Study of rPA102 Formulations with 250 μg aluminum (25° C.) | | | |
|---|---|---|---|
| Test | 100 μg rPA102/ 250 μg Al | 50 μg rPA102/ 250 μg Al | 25 μg rPA102/ 250 μg Al |
| | Results, t = 0 | | |
| Appearance | White suspension | White suspension | White suspension |
| Free rPA102, μg/mL (%)*** | 56 (56) | 18 (36) | 4 (16) |
| pH | 6.86 | 6.92 | 6.96 |
| Relative Potency (mouse relative potency test) | 2.09 | 1.47 | 1.11 |
| FFF (%) | 96.6% | 96.6% | 109.4% |
| | Results (25° C.), t = 1 month | | |
| Appearance | White suspension | White suspension | White suspension |
| Free rPA102, μg/mL (%)*** | 33 (33) | 6.5 (13) | 4 (16) |
| pH | 6.93 | 6.95 | 6.97 |
| Relative Potency (mouse relative potency test) | 1.90 | 1.83 | 1.18 |
| FFF (%) | 95.5% | 93.4% | 101.2% |
| | Results (25° C.), t = 3 months | | |
| Appearance | White suspension | White suspension | White suspension |
| Free rPA102, μg/mL (%)*** | 44 (44) | 12 (24) | 3.2 |
| pH | 7.06 | 6.98 | 6.96 |
| Relative Potency (mouse relative potency test) | 1.10 | 1.20 | 0.63 |
| FFF (%) | 86.7% | 89.% | 93% |
| | Results (25° C.), t = 6 months | | |
| Appearance | * | * | * |
| Free rPA102, μg/mL (%)*** | * | * | * |
| pH | * | * | * |
| Relative Potency (mouse relative potency test) | * | 0.87 | ** |
| FFF (%) | * | * | * |

* = Not Performed at this Time Point

** = Results Not Available

***= Percentage free rPA is a function of the concentration of the unbound rPA divided by the concentration of rPA formulated with Alhydrogel Relative potency is assessed by a mouse Relative Potency test. The mouse Relative Potency test utilizes three components: mouse vaccination and serum collection, serum testing by the Toxin Neutralization Assay and analysis of data to assign the test vaccine potency. Based on available data collected for five reference vaccine samples stored at t=0, 1 and 3 months at 2-8° C., the CV of the mouse relative potency test is estimated to be approximately 15%. Mouse relative potency data for the vaccine formulation containing 50 μg rPA/750 μg aluminum indicates that this formulation is stable when stored for up to 6 months at 2-8° C. and 25° C. Available mouse relative potency data for the remaining formulations containing 750 μg aluminum indicate that they are stable when stored for up to 3 months at 2-8° C. (6 month stability data not yet available). Formulations containing 100 μg rPA exhibited an approximate 50-60% decrease in relative potency when stored for 3 months at 25° C.; these formulations also contained relatively high levels of unadjuvanted ("free") rPA (≥10% w/v).

Formulations containing 250 μg aluminum contained also relatively high levels of free PA (16-57% w/v free rPA) compared to formulations containing 750 μg aluminum (3-10% w/v free rPA). Formulations were selected to maximize stability and to minimize free rPA to enhance manufacturing consistency (i.e., contain <10% of unadjuvanted rPA). Based on these observations the following formulations were selected: 25, 50 and 75 μg of rPA per 750 μg aluminum.

Example 7

Selection of a Preservative

Since multi-dose vials require a preservative, further developmental studies are required. We have identified two preservatives, benzethonium chloride (phemerol) and 2-phenoxyethanol that are used in licensed multi-dose vaccines. BioThrax contains benzethonium chloride, and therefore, we have experience with this preservative. We will initially conduct antimicrobial effectiveness testing on each of these two preservatives in the rPA anthrax vaccine to determine what level of each of the preservatives is required in the vaccine. Antimicrobial effectiveness testing is followed by a formulation study, which is used to down-select to one of the two preservatives. A stability study is then completed to demonstrate that the rPA anthrax vaccine containing the preservative is stable.

2-Phenoxyethanol and benzethonium chloride are tested for minimum acceptable levels which are defined as the ability of the preservative to pass acceptance criteria for USP51. rPA will be formulated to contain concentrations of either 2-phenoxyethanol or benzethonium chloride in either the alanine buffer or the glycine buffer, as described in FIG. 21. AME testing will be executed. In addition, we will determine the lower limits of quantitation and variability of the assays to measure preservative levels. This study will allow us to determine the amounts of 2-phenoxyethanol and benzethonium chloride to use in the formulation studies.

Formulation studies for rPA anthrax vaccine focus on two primary areas: 1) the effect of each of the preservatives on the binding isotherm between rPA and Alhydrogel, and 2) the effect of each of the preservatives on the stability of the rPA102 under accelerated degradation conditions. The initial studies focus on determining if the addition of preservative alters the amount of rPA that is bound per mg of aluminum.

After analysis of the binding isotherm in the presence of preservative, a series of experiments will be performed to examine stability of rPA under forced degradation conditions. Forced degradation of the rPA in formulation buffer containing excipient will be conducted at temperatures of 25 and 35° C. All formulations will be tested using release assays as well as by the additional characterization assays described in FIG. 22.

The rPA in the vaccine will be analyzed using standard physicochemical methods including front faced fluorescence, epitope exposure, native elutability, relative levels of bound versus free rPA, and physical structure of the rPA measured by SDS-PAGE and peptide digest with detection by mass spectrometry (MS). Specific deamidation sites on the rPA will be identified using peptide digest followed by liquid chromatography-mass spectrometry (LC-MS), while deamidated residues will be identified by mass spectrometry-mass spectrometry (MS-MS).

The study on the stability of rPA under forced degradation conditions will be performed over one month. Selection of a preservative will be based on a combination of the results of the initial antimicrobial effectiveness testing and the effects of each preservative on the relative stability of the rPA. The baseline for comparison of the effects of preservative on formulated rPA will be, for example, a vaccine comprising approximately 200 μg/mL rPA102 and approximately 0.5 mg/mL aluminum hydroxide, formulated using the alanine and glycine based buffers without preservative.

A stability study will be performed using the preservative selected from the prior two studies. The rPA anthrax vaccine will be formulated in alanine with the selected preservative. The formulations and testing schedule is presented in FIG. 23.

What is claimed is:

1. A stable vaccine for stimulating an immune response to a *Bacillus anthracis* protective antigen comprising:

a) a purified *B. anthracis* protective antigen protein;

b) an alanine formulation buffer; and c) a pharmaceutically acceptable adjuvant.

2. The vaccine of claim 1, wherein said alanine formulation buffer comprises about 50 to 500 mM alanine.

3. The vaccine of claim 1, wherein said alanine formulation buffer comprises about 220 mM alanine, about 25 mM sodium phosphate and about 0.01% polysorbate 80.

4. The vaccine of claim 1, wherein said alanine formulation buffer further comprises glycine and/or proline.

5. The vaccine of claim 1, wherein said alanine formulation buffer is at about pH 6.2-8.0.

6. The vaccine of claim 1, wherein said adjuvant is selected from the group consisting of alhydrogel, CpG, an immunostimulatory sequence (ISS) and calcium phosphate.

7. The vaccine of claim 6, wherein said adjuvant is Alhydrogel.

8. The vaccine of claim 7, wherein said vaccine comprises about 750 μg aluminum.

9. The vaccine of claim 1, wherein said purified *B. anthracis* protective antigen protein is produced from an asporogenic *B. anthracis* bacterium.

10. The vaccine of claim 9, wherein said asporogenic *B. anthracis* bacterium is a ASterne-1(pPA102)CR4 strain of bacteria.

11. The vaccine of claim 1, wherein said purified *B. anthracis* protective antigen protein comprises amino acids 30-735 of SEQ ID NO: 1.

12. The vaccine of claim 11, wherein said purified *B. anthracis* protective antigen protein comprises SEQ ID NO: 1.

13. The vaccine of claim 1, wherein said vaccine comprises at least about 25 μg purified *B. anthracis* protective antigen protein.

14. The vaccine of claim 1, wherein said vaccine comprises at least about 25 μg purified *B. anthracis* protective antigen protein and about 750 μg aluminum.

15. A method of preventing or treating an anthrax disease comprising administering a pharmaceutically effective amount of the vaccine of claim 1 to a subject.

16. The method of claim 15, wherein said anthrax disease is inhalation anthrax.

17. A method of inducing an immune response in a subject comprising administering to the subject a vaccine of claim 1.

18. A method of vaccinating a subject against anthrax comprising administering to the subject a vaccine of claim 1.

19. The vaccine of claim 1, wherein the vaccine is a liquid solution or suspension.

* * * * *

SEQUENCE LISTING

```
<160> NUMBER OF SEQ ID NOS: 2

<210> SEQ ID NO 1
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
```

-continued

```
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685
```

-continued

```
Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Lys Lys Arg
1
```